United States Patent [19]
Pang et al.

[11] Patent Number: 5,296,195
[45] Date of Patent: Mar. 22, 1994

[54] AUTOMATIC IMMUNOCHEMISTRY ANALYZING APPARATUS AND METHOD

[75] Inventors: Wings S. Pang, West Covina; Peter Kan, Fullerton; George K. Shibata, Chino, all of Calif.

[73] Assignee: Beckman Instruments, Inc., Fullerton, Calif.

[21] Appl. No.: 956,049

[22] Filed: Oct. 2, 1992

Related U.S. Application Data

[62] Division of Ser. No. 512,036, Apr. 30, 1990, Pat. No. 5,162,236.

[51] Int. Cl.$^5$ .................. G01N 21/47; G01N 33/00
[52] U.S. Cl. .................. 422/82.05; 422/68.1; 422/109; 435/290; 435/808; 436/147; 436/909
[58] Field of Search ............ 435/3, 4, 7.1, 808, 435/289, 290; 436/147, 909, 807–809, 536, 517; 422/68.1, 82.12, 109, 82.05

[56] References Cited

U.S. PATENT DOCUMENTS

| | | | |
|---|---|---|---|
| 3,616,264 | 10/1971 | Ray et al. | 435/290 |
| 4,086,061 | 4/1978 | Hoffa et al. | 422/50 |
| 4,157,871 | 6/1979 | Anderson et al. | 356/341 |
| 4,200,607 | 4/1980 | Suzuki | 422/64 |
| 4,204,837 | 5/1980 | Sternberg et al. | 436/517 |
| 4,268,171 | 5/1981 | Sternberg | 436/517 |
| 4,299,796 | 11/1981 | Hogen Esch | 422/63 |
| 4,322,216 | 3/1982 | Lillig et al. | 436/47 |
| 4,323,537 | 4/1982 | Mody | 422/63 |
| 4,401,387 | 8/1983 | Tokinage | 356/341 |
| 4,419,444 | 12/1983 | Quash | 435/7 |
| 4,518,700 | 5/1985 | Stephens | 436/52 |
| 4,539,295 | 9/1985 | Blough, Jr. | 436/34 |
| 4,835,110 | 5/1989 | Seymour et al. | 436/517 |
| 5,082,790 | 1/1992 | Theobold et al. | 436/536 |

FOREIGN PATENT DOCUMENTS 0049509 4/1982 European Pat. Off. .

OTHER PUBLICATIONS

Anderson, R. J. and Sternberg, J. C., "A Rate Nephelometer for Immunoprecipitin Measurement of Specific Proteins", *Automated Immunoanalysis, Part II*, Ritchie (ed.), Marcel Dekker, Inc., Ch. 19, pp. 409–469 (1978).

*Primary Examiner*—James C. Housel
*Assistant Examiner*—Robert Carpenter
*Attorney, Agent, or Firm*—William H. May; Gary T. Hampson; Charles Berman

[57] ABSTRACT

A system for analyzing a chemical reaction provides control of the temperature and volume of the reagents to improve the accuracy and precision in quantitative measurements of specific proteins and other immunochemistries in body fluids. The reaction occurs in a cuvette within a nephelometric optics module. A sensor senses the temperatures of reaction buffer liquids as they flow into the cuvette, and a heat exchanging device increases or decreases the temperatures of the buffer liquids. A control circuit responsive to the temperature sensor controls the heat exchanging device to maintain the temperature of the buffer liquids and the cuvette within a selected temperature range. The system may also include a sample pickup station, a sample probe for withdrawing a selected sample from the sample pickup station, a sample preparation station, and transport device for carrying said sample from the sample preparation station to the reaction cuvette. The system may include an antibody pickup station, an antibody probe for withdrawing an antibody from the antibody pickup station, an antibody preparation station, and antibody transport device for carrying the antibody from the antibody preparation station to the reaction cuvette.

24 Claims, 14 Drawing Sheets

| PICK UP SAMPLE FROM CELL 134A |
| ASPIRATE DILUTION DILUENT |
| MOVE PROBE TO CELL 134B |
| DISPENSE SAMPLE AND DILUENT |
| MIX SAMPLE AND DILUENT IN CELL 134B |
| PICK UP DILUTED SAMPLE FROM CELL 134B |
| ASPIRATE DILUENT |
| MOVE PROBE TO CELL 134C |
| DISPENSE DILUTED SAMPLE AND DILUENT |
| MIX DILUTED SAMPLE AND DILUENT |
| WASH PROBE |

TO

AUTOMATIC IMMUNOCHEMISTRY ANALYZING APPARATUS AND METHOD

This is a division of the application Ser. No. 07/512,036, filed Apr. 30, 1990 and issued as U.S. Pat. No. 5,162,236.

BACKGROUND OF THE INVENTION

The invention relates generally to immunochemistry analyzing apparatus and methods and particularly to rate nephelometric techniques for analyzing precipitate forming reactions between antigens and antibodies.

Certain analytes, such as proteins, in body fluids may be detected by monitoring chemical reaction between the analytes and antibodies produced in goats, rabbits, etc. In particular, polyvalent protein antigens in sera may react with their corresponding antibodies to produce precipitates. Such antibodies are called precipitins, and their reactions are called immunoprecipitin reactions. In these reactions the amount of precipitate is a function of either the antibody concentration or the antigen concentration, depending upon the relative concentrations of the antigen and antibody.

Nephelometry involves measuring the intensity of light scattered by particles in suspension in a cell when a beam of light is passed through the cell. Rate nephelometry is the monitoring of the rate of change of the amount of light scattered as a reaction proceeds. The resulting complexing and consequent changing scattered light intensity occurs at a rate that increases gradually at first. The rate then increases rapidly until it reaches a peak rate before it decreases to zero as either the antibody or the antigen is depleted.

The analyzer electronics derives the peak value of the rate of change from the scattered light signal. For these purposes, an antigen-antibody immunoprecipitin reaction is conducted in an optically transparent sample container or vial. An excitation system directs a beam of light into the sample container, and a detection system measures light scattered at a forward angle from the precipitate. The detected nephelometric, or light scatter, signal is differentiated to provide a function indicated of the rate. The peak value of the rate is indicative of the concentration of the desired antigen or antibody.

Although less sensitive than enzyme immunoassay, fluorescent immunoassay and radioimmunoassay, nephelometry and rate nephelometry provide the most convenient and direct method for measuring most clinically significant proteins. Nephelometric measurements require no labels and provide direct real time monitoring of the antigen-antibody reaction.

The basis for nephelometric determination of antigens and antibodies is the formation of molecular aggregates when the bivalent antibody molecules combine with multivalent antigen molecules. When the connections of the antigens and antibodies are near equivalence, considerable cross linking occurs between the molecules. Antibody molecules bridge between antigen molecules to link several antigen molecules and many antibody molecules into large molecular aggregates that from a precipitate.

These molecular aggregates, after attaining molecular weights of about 3 million or greater, scatter an appreciable amount of light, which may be monitored with various means for detecting light. When the antibody is present in considerable excess, only small scattering centers develop because each antigen tends to have its sites saturated with antibody molecules. The probability that a single antibody molecules will from a bridge between two antigen molecules is small. The reaction forms complexes of the form $Ag(Ab)_m$, where Ag represents the antigen, Ab represents the antibody and m is the valency of the antigen; but larger complexes do not form. No precipitation occurs in extreme antibody excess.

In the case of antigen excess, each antibody molecule has both of its sites occupied by different molecules. Complexes of the form $(Ag)_2Ab$ form, but there are insufficient antibody molecules to bridge between the antigen molecules to form a cross linked lattice.

In the case of antibody excess, or low antigen concentration, no free antigen molecules appear in the supernatent, and an increasing amount of precipitation occurs as antigen is added to the sample. On a plot of peak rate versus antigen concentration, the peak rate increases from zero to a maximum and then decreases from the maximum with further increases in antigen concentration. On the ascending portion of the curve, at lower antigen concentrations, there is an excess of antibody. As further antigen is added, the system moves into antigen excess such that the antigen ties up all the antibody molecules without cross linking. There is a decrease in the total amount of precipitation, and no free antibody is found in the supernatent.

The double valued nature of the functional relationship between the antigen concentration and the amount of precipitate formed presents problems in measurement because a given amount of precipitate can correspond to both a low amount and a high amount of antigen. The measuring range in nephelometry is preferably on the ascending region of the curve where there is an excess amount of antibody. Only measurements in the ascending region of the curve provide reliable data on the amount of antigen present in a sample. Clinical applications of nephelometry generally require analysis of a large number of samples. Therefore, the time required for measuring each sample is an important consideration.

After a measurement has been made in the ascending portion of the curve, it is necessary to verify that the peak rate obtained was valid. The time required for this verification is called the peak verify time. If it is determined that a measured peak rate corresponds to a higher antigen concentration on the descending portion of the curve in antigen excess, it is necessary to dilute the sample and remeasure the rate for the sample. The dilutions and remeasuring are repeated until a peak rate in antibody excess is obtained. After an acceptable peak rate measured in antibody excess is derived from the diluted sample, the corresponding antigen concentration is scaled upward by the appropriate dilution factor to determine the actual antigen concentration of the original sample.

There are several publications describing nephelometric assay of antigen-antibody reactions and addressing the problems encountered in determining the antigen or antibody excess condition of such reactions. These publications include: (1) Savory et al., Kinetics of the lgG-anti-lgG Reaction as Evaluated by Conventional and Stopped-flow Nephelometry, *Clin. Chem.*, 20, 1071 (1974); (2) Buffone et al., Use of a Laser-equipped Centrifugal Analyzer for Kinetic Measurement of Serum lgG. *Clin. Chem.*, 20, 1320 (1974); (3) Buffone et al., Evaluation of Kinetic Light Scattering as an Approach to the Measurement of Specific Proteins With the Centrifugal Analyzer. I. Methodology. *Clin. Chem.*, 21. 1731 (1975); (4) Buffone et al., Evaluation of Kinetic Light Scattering as an Approach to the Measurement of Specific Proteins With the Centrifugal Analyzer. II. Theoretical Considerations. *Clin. Chem.*, 21, 1735 (1975); (5) Tiffany et al., Specific Protein Analysis by Light-scatter Measurement With a Miniature Centrifugal Fast Analyzer. *Clin. Chem.*, 20, 1055 (1974); (6) Anderson et al., A Rate Nephelometer for Immunoprecipitin Measurement of Specific Serum Proteins in Automated Immunoanalysis, 2, R. F. Ritchie, Ed., Marcel Dekker, New York (1978), pp 409-469; and (7) Sternburg, Monitoring the Precipitin Reaction Using Rate Nephelometry, ACPR 27, April, (1984).

Savory et al., *Clin. Chem.*, 20, 1071 (1974) and Buffone et al., *Clin. Chem.*, 20, 1320 (1974) disclose a two-point semi-kinetic method for measuring specific proteins by deriving the average rate of change of scatter between two fixed times. These references disclose the scatter intensity rises more rapidly in comparison with the end value that it approaches in antigen excess than in antibody excess. These references neither disclose nor suggest any method for utilizing such behavior for determining an excess of antibody or antigen.

Buffone et al., *Clin. Chem.*, 21. 1731 (1975) and Buffone et al., *Clin. Chem.*, 21, 1735 (1975) disclose that consideration of later time intervals with the use of both PBS and PEG-PBS demonstrate no unique characteristics on which differentiation of either antigen or antibody excess samples could be used and that the kinetic procedure cannot directly detect antigen excess. Therefore, although the fundamental properties of antigen-antibody reactions are disclosed, these references fail to disclose kinetic methods for determining antigen or antibody excess.

Tiffany et al., *Clin. Chem.*, 20, 1055 (1974) reports a study of kinetic and equilibrium measurement of antigen-antibody reactions and the achievement of better precision with equilibrium measurements. Tiffany et al. disclose a method for determining antigen excess for equilibrium measurements by measuring a change in equilibrium light scatter intensity caused by the post-addition of a small quantity of antibody into the reaction cell after the primary antigen-antibody reaction has reached equilibrium. If the primary antigen-antibody reaction proceeded in an antigen excess condition, and additional antibody is injected into the reaction cell containing the equilibrated reaction components, the excess antigen reacts with the injected antibody and produces a significant change in scatter intensity. On the other hand, if the primary antigen-antibody reaction proceeded in antibody excess, subsequent injection of the additional antibody produces an insignificant response.

Although determination of antigen or antibody excess by post addition of reactant into the primary reaction is a reliable technique, it is time consuming to perform. Consequently, a time delay is introduced while waiting for the primary reaction to reach equilibrium before the post addition step.

U.S. Pat. No. 4,157,871 to Anderson et al. discloses several kinetic methods for determining antigen excess. In one such method, the peak rate value and the elapsed time from the start of a reaction to occurrence of the peak rate are graphed as functions of increasing antigen concentration for a fixed antibody concentration. A coordinate transformation is used to derive a single valued function, derived from the peak rate and the time thereto, for distinguishing antigen excess.

In a second method disclosed by U.S. Pat. No. 4,157,871 the rate signal, which is the first derivative of the nephelometric signal, is differentiated to generate the second derivative of the nephelometric signal. The elapsed time from the start of the reaction to the occurrence of the peak of the rate signal is determined together with the time difference between the peak value of the rate signal and the peak value of the second derivative signal. A ratio that distinguishes between antigen excess and antibody excess is established by dividing the elapsed time to the peak rate by the time difference between the peak values of the first and second derivative signals.

U.S. Pat. No. 4,204,837 to Sternberg et al. discloses a method of nephelometric analysis of antigen-antibody reactions to determine whether the reaction is in an antigen excess or antibody excess condition. A first reaction between antigen and antibody reaction components is initiated, and the rate of change of a nephelometric signal is derived from the reaction to develop a rate signal. The peak value of the rate signal provides a measure of the antigen concentration. Sternberg et al. disclose that the rate signal provides kinetic information for may samples from which the antigen or antibody excess condition of the first reaction can be determined without requiring a further step of post-addition of antigen or antibody to the reaction.

Sternberg et al. disclose normal measuring range of peak values between upper and lower thresholds that defines an ambiguous zone for peak values for which a reaction may be in either antigen or antibody excess. Samples having peak heights greater than the threshold can immediately be eliminated for being greater than the normal measuring range, i.e. rejected as being clearly in antigen excess, or as being in near equivalence whether on the antibody or antigen side of the kinetic equivalence point. Sternberg et al. disclose that samples having a peak height lower than the lower threshold are regarded as being clearly on the antibody excess portion of the response curve since it is unlikely that antigen excess samples in a physiological feasible range will exhibit peak heights lower than the lower threshold. The method of Sternberg et al. does not require a post addition step for samples exhibiting peak values below the lower threshold for determining the antigen or antibody excess condition. Similarly, samples exhibiting peak heights above the threshold do not require post-addition. Such samples are rejected, and the reaction is repeated at a higher dilution, or lower concentration, of antigen. The step of post addition for determining the antigen or antibody excess condition is required only for samples having peak heights in the ambiguous zone.

U.S. Pat. No. 4,322,216 to Lillig et al. discloses a method and apparatus for conveying liquids to and from a reaction cell in an automated sample handling instrument. Lillig et al. disclose a track and one or more cars mounted thereon. One car carries a sample to a diluting well; a second car transfers the diluted sample to a reaction cell; and a third car transfers a reagent to the reaction cell. Sensors on the track detect when the cars are properly positioned relative to a plurality of slots in the track.

SUMMARY OF THE INVENTION

The present invention provides a system for analyzing a reaction between a pair of reagents that overcomes difficulties associated with previous systems. The present invention provides improved accuracy and precision in quantitative measurements of specific proteins and other immunochemistries in body fluids with improved throughput over the prior art.

The invention employs a reaction cuvette, which preferably is within a nephelometric optics module for containing the reagents during the reaction. The reagents are delivered to the reaction cuvette with precise control of the temperature. A sensor senses the temperatures of reaction buffer liquids as they flow into the cuvette, and a heat pump device, which preferably operates using the Peltier effect, increases or decreases the temperatures of the reaction. A control circuit responsive to the temperature sensor controls the heat exchanging device to maintain the temperature of the buffer liquids and the cuvette within a selected temperature range.

The temperature sensor preferably comprises a thermistor in thermal contact with the cuvette and liquids flowing into the cuvette.

The system of the present invention is particularly suited to analyzing reactions in which the first reagent comprises an antigen and the second reagent comprises an antibody. The reaction cuvette is preferably positioned within an nephelometer such that the reaction rate of the antigen and antibody may be monitored by processing light scattered from the reaction.

The system may also comprise a sample pick up station, sample probe means for withdrawing a selected sample from the sample pick up station, a sample preparation station for receiving the sample, and sample transport means for carrying the sample from the sample preparation station to the reaction cuvette.

The sample transport means preferably comprises at least one rail, a sample probe carriage slidably mounted on the rail, first stepper motor means for controlling the position of the sample probe carriage along the rail, and first position sensor means for sensing when the sample probe carriage is adjacent a first reference point fixed relative to the rail.

The sample transport means further preferably comprises second stepper motor means mounted to the sample probe carriage for moving the sample probe means perpendicular to the rail, the sample probe means being movable between a retracted position for selectively establishing fluid communication with the sample station, the reaction cuvette and a sample probe wash station and an extended position for moving the sample probe means between the sample station, the reaction cuvette and the sample probe wash station, and second position sensor means for sensing when the sample probe means is in the extended position.

The system of the invention also preferably comprises an antibody pick up station, antibody probe means for withdrawing an antibody from the antibody pick up station, an antibody preparation station for receiving the antibody, and antibody transport means for carrying the antibody from the antibody preparation station to the reaction cuvette.

The antibody transport means may comprise the rail, an antibody probe carriage slidably mounted on the rail, third stepper motor means for controlling the position of the antibody probe carriage along the rail, and third position sensor means for sensing when the antibody probe carriage is adjacent a second reference point fixed relative to the rail.

The antibody transport means may further comprise fourth stepper motor means mounted to the antibody probe carriage for moving the antibody probe means perpendicular to the rail, the antibody probe means being movable between a retracted position for selectively establishing fluid communication with the antibody pickup station, the reaction cuvette and a antibody probe wash station and an extended position for moving the antibody probe means between the anitbody station, the reaction cuvette and the antibody probe wash station, and fourth position sensor means for sensing when the antibody probe means is in the extended position.

The method of the invention for analyzing a reaction between reagents comprises the steps of injecting the reagents into a reaction cuvette for containing the reagents during the reaction; and controlling the temperature of the reagents within a selected temperature range.

The method of the invention preferably includes the steps of sensing the temperature of the reactioin cuvette with first temperature sensor means; increasing or decreasing the temperatures of the reaction cuvette with first heat pumping means; and activating the first heat pumping means in response to the first temperature sensor means to maintain the temperature of the reaction cuvette within a selected temperature range.

The method of the invention may further include the steps of sensing the temperature of the first and second reagent delivery means with second temperature sensor means; increasing or decreasing the temperatures of the reagents with second heat pumping means for selectively; and activating the second heat pumping means in response to the second temperature sensor means to maintain the temperature of the first and second reagents within the selected temperature range.

The step of delivering the first reagent to the cuvette may comprise the steps of aspirating a selected sample into a sample probe from a sample pick up station and transporting the sample from the sample preparation station to the reaction cuvette. The method of the invention also preferably further includes the steps of mounting a sample probe carriage slidably on a rail; controlling the position of the sample probe carriage along the rail with first stepper motor means; and sensing when the sample probe carriage is adjacent a first reference point fixed relative to the rail.

The method of the invention may further comprise the steps of moving the sample probe means perpendicular to the rail with second stepper motor means to the sample probe carriage between a retracted position for selectively establishing fluid communication with the sample station, the reaction cuvette and a sample probe wash station and an extended position for moving the sample probe means between a sample station, the reaction cuvette and the sample probe wash station; and sensing when the sample probe means is in the extended position.

The step of delivering the second reagent preferably comprises the steps of aspirating an antibody from an antibody pick up station into an antibody probe; and transporting the antibody to the reaction cuvette. The step of delivering the second reagent may further comprise the steps of mounting an antibody probe carriage slidably on the rail; controlling the position of the antibody probe carriage along the rail with third stepper motor means; and sensing when the antibody probe carriage is adjacent a second reference point fixed relative to the rail.

The step of delivering the second reagent may further comprise the steps of mounting fourth stepper motor means to the antibody probe carriage for moving the antibody probe means perpendicular to the rail between a retracted position for selectively establising fluid communication with the antibody pickup station, the reaction cuvette and a antibody probe wash station and an extended position for moving the antibody probe means between the antibody station, the reaction cuvette and the antibody probe was station; and sensing when the antibody probe means is in the extended position.

The method of the present invention may further comprise the steps of forming the first reagent to comprise an antigen; forming the second reagent to comprise an antibody; and positioning the reaction cuvette within a nephelometer such that the reaction of the antigen and antibody may be monitored by processing light scattered from the reaction.

DESCRIPTION OF THE PREFERRED EMBODIMENT

Immunochemistry Analyzer Apparatus

A. Mechanical Components.

Figure 1:
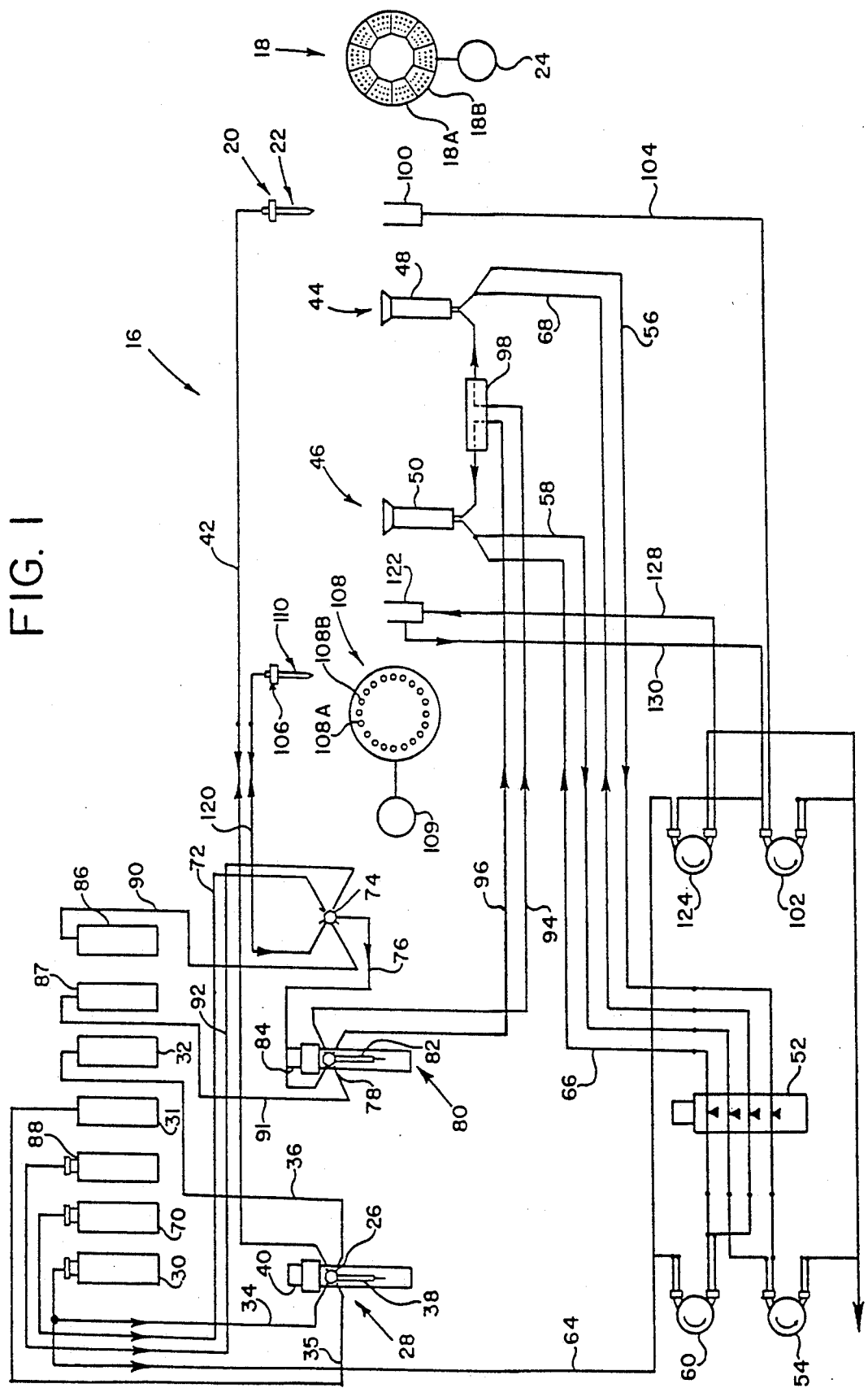
FIG. 1 schematically illustrates an analyzer apparatus according to the present invention.

Referring to FIG. 1, an analyzer system 16 according to the present invention analyzes samples held in a sample turntable 18. Sample turntable 19 includes a plurality of segments 18A, 18B, etc. for holding samples of selected dilution. A transport mechanism 20, best shown in FIGS. 4-7, carries a sample probe 22 to a position above sample turntable 18, which rotates to place a selected sample under sample probe 22. A stepper motor 24 drives the sample turntable to place the selected sample in position for sample probe 22 to be positioned over the sample.

A sheer valve 26 in a sample diluter/dispenser 28 opens to receive a selected diluent from reservoirs 30-32 connected to shear valve 26 via fluid lines 34-36, respectively. Shear valve 26 preferably is actuated by an AC motor (not shown in FIG. 1). Sample diluter/dispenser 28 includes a syringe 38 for receiving the diluent and a drive motor 40 for actuating syringe 38. A sample diluter/dispenser suitable for use in system 16 is sold under the trademark ACCU-PREP by Beckman Instruments, Inc., assignee of the present invention. A fluid line 42 places syringe 38 in fluid communication with sample probe 22 for mixing the diluent with the sample.

Sample probe 22 injects a diluent to make an appropriate dilution, such as 1:36 or 1:216, to the selected sample. The antigen in the sample will be reacted with an antibody in either a nephelometric optics module 44 or a nephelometric optics module 46. The reaction occurs in a cuvette 48 in nephelometric optics module 44 or in a cuvette 50 in nephelometric optics module 46. Reaction cuvettes 48 and 50 are shown schematically in FIG. 1 and cuvette 48 is shown in greater detail in FIG. 3.

Cuvettes 48 and 50 are ordinarily operated independently of one another. The selected cuvette for a reaction is washed before placement of reagents therein. In order to wash cuvettes 48, a pinch valve 52 opens, and an optics drain pump 54 starts to drain cuvette 48 fluid lines 56. Cuvette 50 is drained through a fluid line 58 that is also connected to pinch valve 52. An optics fill pump 60 is activated to pump a wash diluent into the selected cuvette via a fluid line 64 connected between reservoir 30 and optics fill pump 60 and fluid lines 66 and 68 that lead from optics fill pump 60 to cuvettes 48 and 50, respectively. Optics drain pump 54 then drains the wash diluent from cuvettes 48 and 50.

A rinse buffer from a reservoir 70 is added to cuvettes 48 and 50. A fluid line 72 is connected between reservoir 70 and a shear valve 74 to carry the rinse buffer thereto. A fluid line 76 carries the buffer between shear valve 74 and a second shear valve 78 in an antibody/buffer dispenser 80, which includes a syringe 82 and an actuator motor 84. Valve 74 selects the fluid to be input to syringe 82 is connected to buffer reservoirs 86 and 88 through fluid lines 90 and 92, respectively. A buffer reservoir 88 is connected to valve 78 through a fluid line 91. Antibody/buffer dispenser 80 has outputs to a pair of fluid lines 94 and 96 that carry the rinse buffer from shear valve 78 through a temperature control module 98 to cuvettes 48 and 50, respectively.

A reaction buffer from reservoirs 86, 87 or 88 is placed in the selected cuvette through fluid lines 90-92, respectively, valve 74, fluid line 76 and valve 78. The reaction buffer then flows to cuvette 48 through fluid line 94 or to cuvette 50 through fluid line 96. In a preferred method using the system 16 to analyze antibody-antigen reactions, 600 µl of the selected reaction buffer is dispensed to the cuvette before the antibody and antigen are dispensed thereto.

In order to mix the sample and the antibody, sample probe 22 picks up the diluted sample from sample turntable 18 and transfers the sample to reaction cuvette 48, for example, although the reaction may be in either cuvette 48 or cuvette 50. The sample is diluted with a diluent that passes from reservoir 30 to shear valve 24 and then through fluid line 42. After delivering the diluted sample to nephelometric optics module 44, transport mechanism 20 moves sample probe 22 to a wash station 100. Wash diluent is pumped through sample probe 22 from reservoir 30. After sample probe 22 is washed, a wash station drain pump 102 drains waste from wash station 100 through a fluid line 104.

Figure 4:
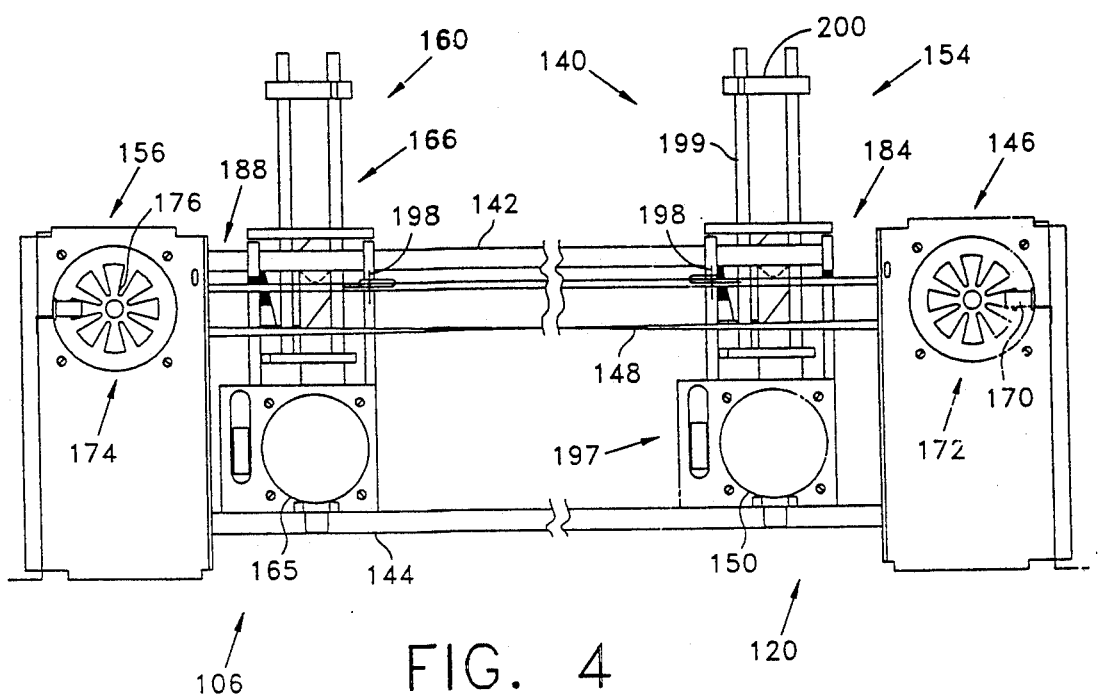
FIG. 4 is an elevation view of transport mechanisms that may be included in the analyzer of FIG. 1.
Figure 5:
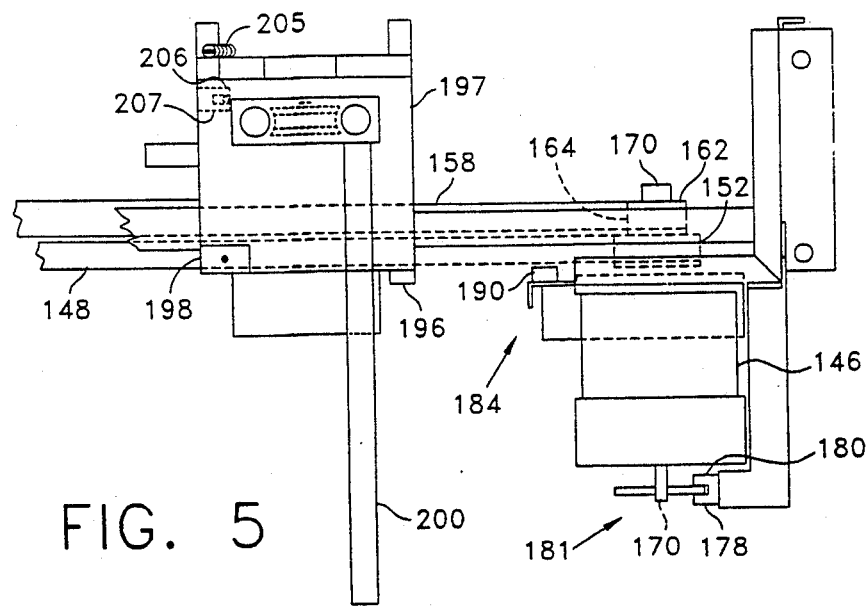
FIG. 5 is a plan view of the transport mechanisms of FIG. 4.
Figure 6:
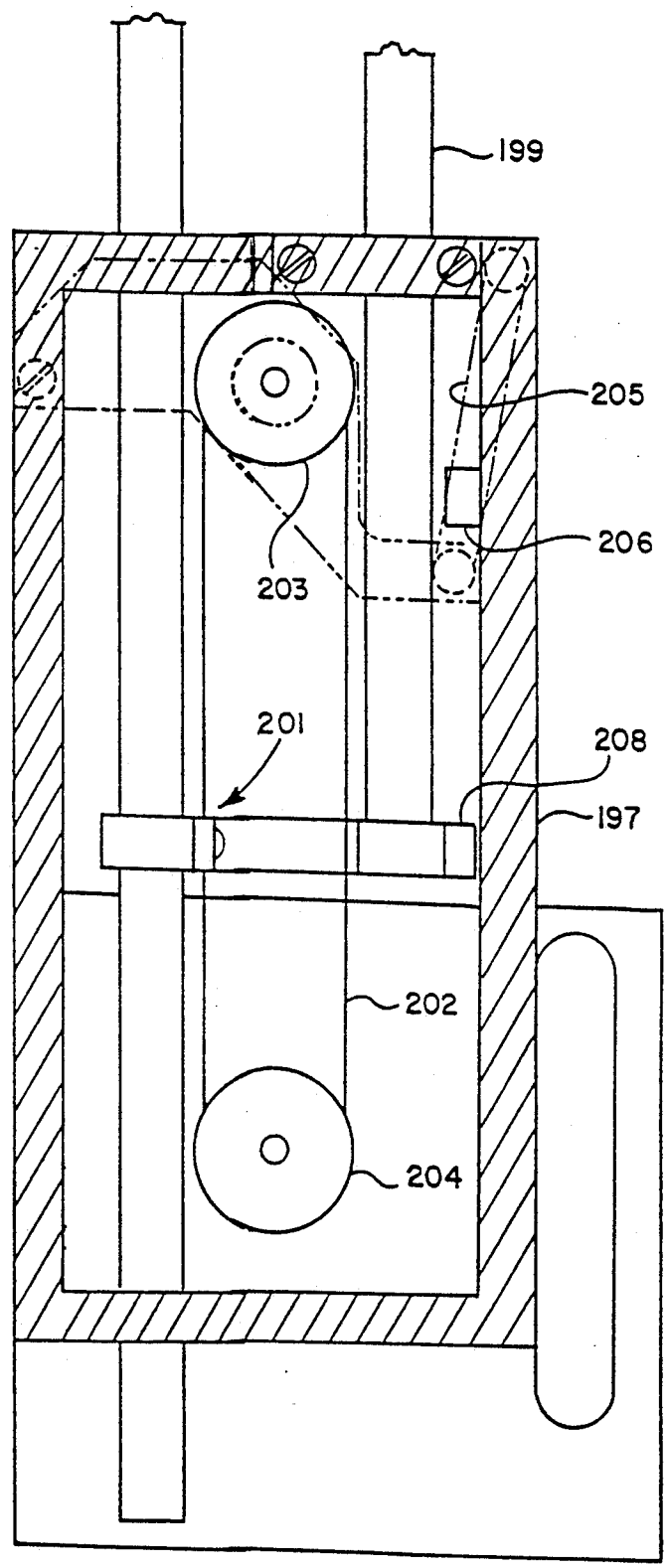
FIG. 6 is an elevation view showing details of a probe carrier mechanism included in FIG. 4.

Placement of the antibody to be analyzed in reaction cuvette 48 or 50 includes moving an antibody probe transport mechanism 106 to an antibody turntable 108. Antibody probe carriage mechanism 106 is shown schematically in FIG. 1 and is best shown in FIGS. 4-6, which are described subsequently. A stepper motor 109 rotates antibody turntable 108 to position a selected antibody vial 108A, 108B, etc. under an antibody probe 110. Syringe 82 acting through valve 78, fluid line 76, valve 74 and a fluid line 120 then aspirates a predetermined volume of the antibody into the antibody probe 110. The antibody may fill antibody probe 110 and extend a short distance into a fluid line 120, which is connected between valve 74 and antibody probe 110.

Antibody probe carriage mechanism 106 carries antibody probe 110 to nephelometric optics module 44, for example, to deliver the antibody reagent thereto. Syringe 82 again acting through valve 78, fluid line 76, valve 74 and a fluid line 120 then dispenses the antibody to cuvette 48.

After delivering the antibody reagent to nephelometric optics module 44 or 46, antibody probe transport mechanism 106 moves to an antibody wash station 122. An antibody probe wash pump 124 pumps wash liquid through a fluid line 128 to antibody probe wash station 122, and wash station drain pump 102 removes the wash diluent from antibody probe wash station 122 through a fluid line 130. Wash diluent may be supplied to antibody probe 110 through fluid line 38, shear valve 74 and fluid line 120. Wash diluent is removed from antibody probe wash station 122 through fluid line 120.

Figure 7:
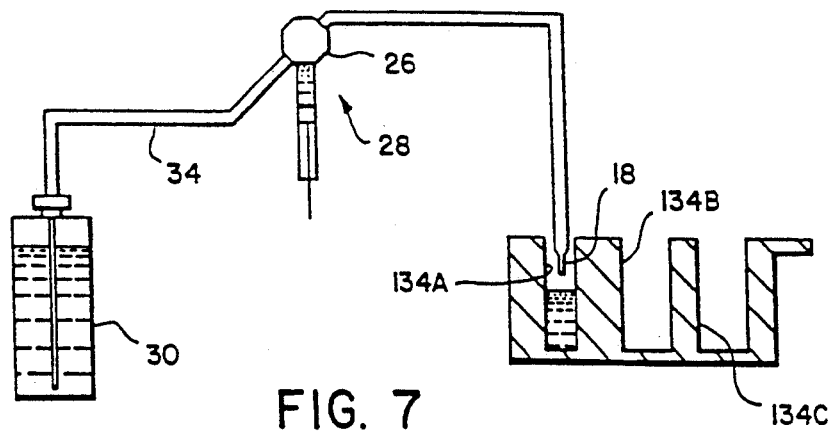
FIG. 7 illustrates a portion of a sample holder that may be included in the apparatus of FIG. 1.

Referring to FIGS. 1 and 7, sample holder portion 18A preferably includes a plurality of lines of cells 134A, 134B and 134C that hold selected dilutions of the sample. For example, cell 134A may contain pure antigen sample, cell 134B may contain the sample and diluent in a 1:36 ratio and cell 134C may contain the sample and diluent in a 1:216 ratio. Sample probe 22 is shown projecting into cell 134A. Fluid line 42 connects sample probe 22 and shear valve 24 in sample diluter/dispenser 60. Fluid line 42 connects shear valve 24 and reservoir 30 to supply diluent to sample diluter/dispenser 28 for mixing with the sample drawn therein through fluid line 42.

Figure 3A:
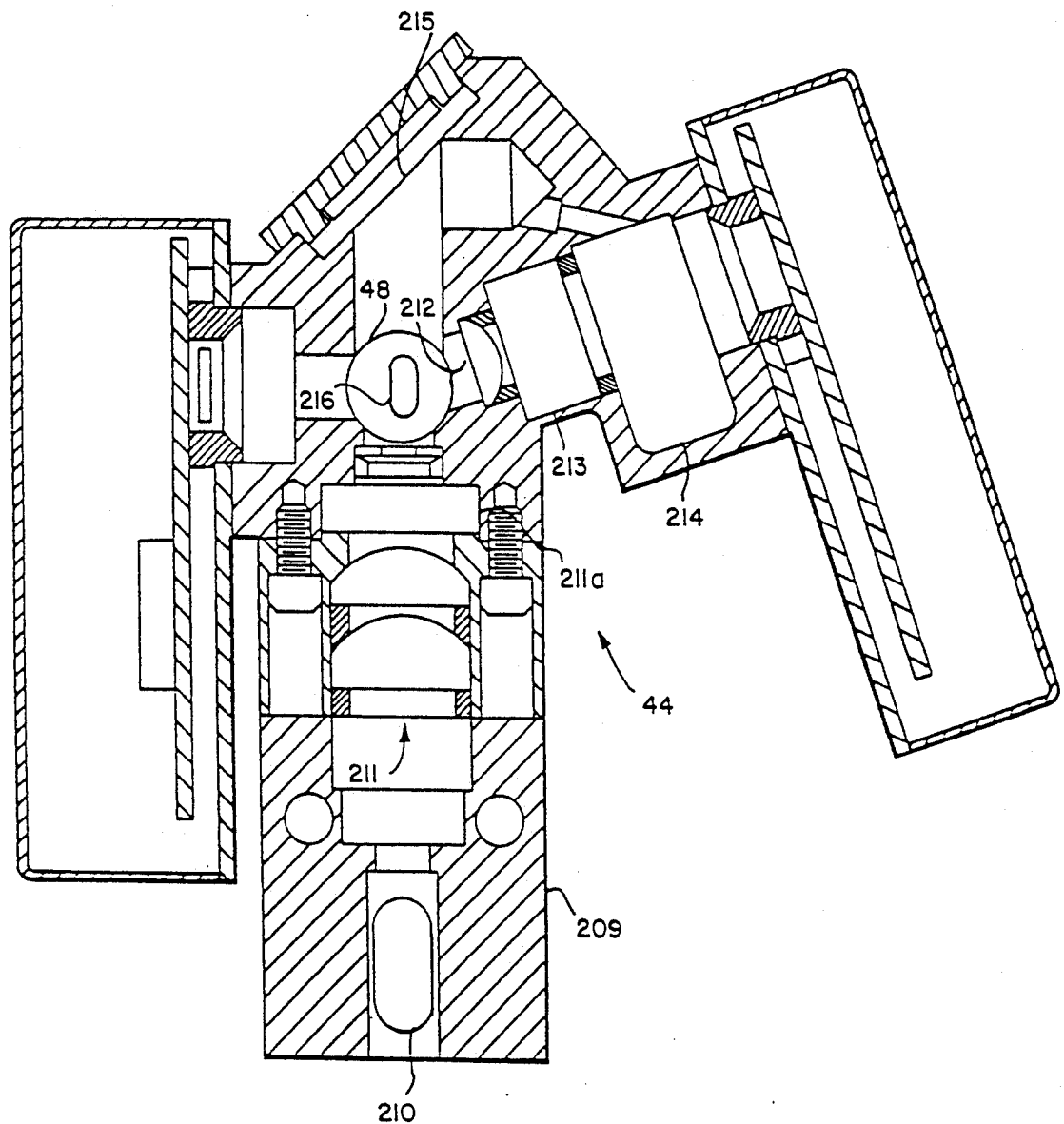
FIG. 3A and 3B illustrate a nephelometer for measuring the light scatter of a reaction between an antibody and its antigen.
Figures 3B, 8B:
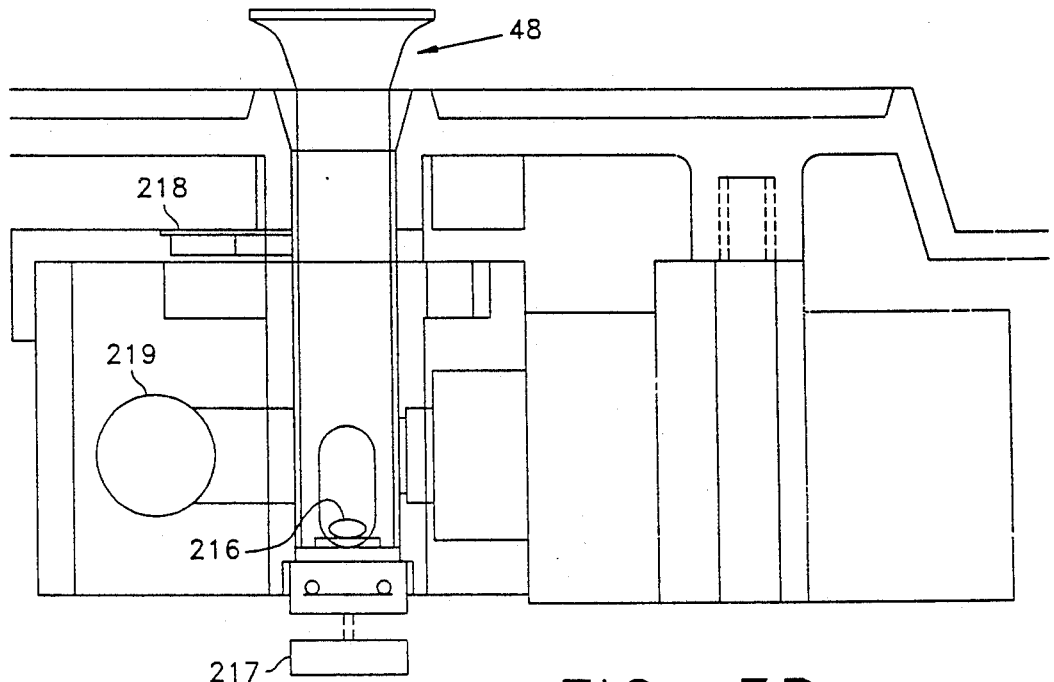
FIGS. 8A and 8B illustrate a process sequences that may used to operate the apparatus of FIGS. 1-7.
Figure 8A:
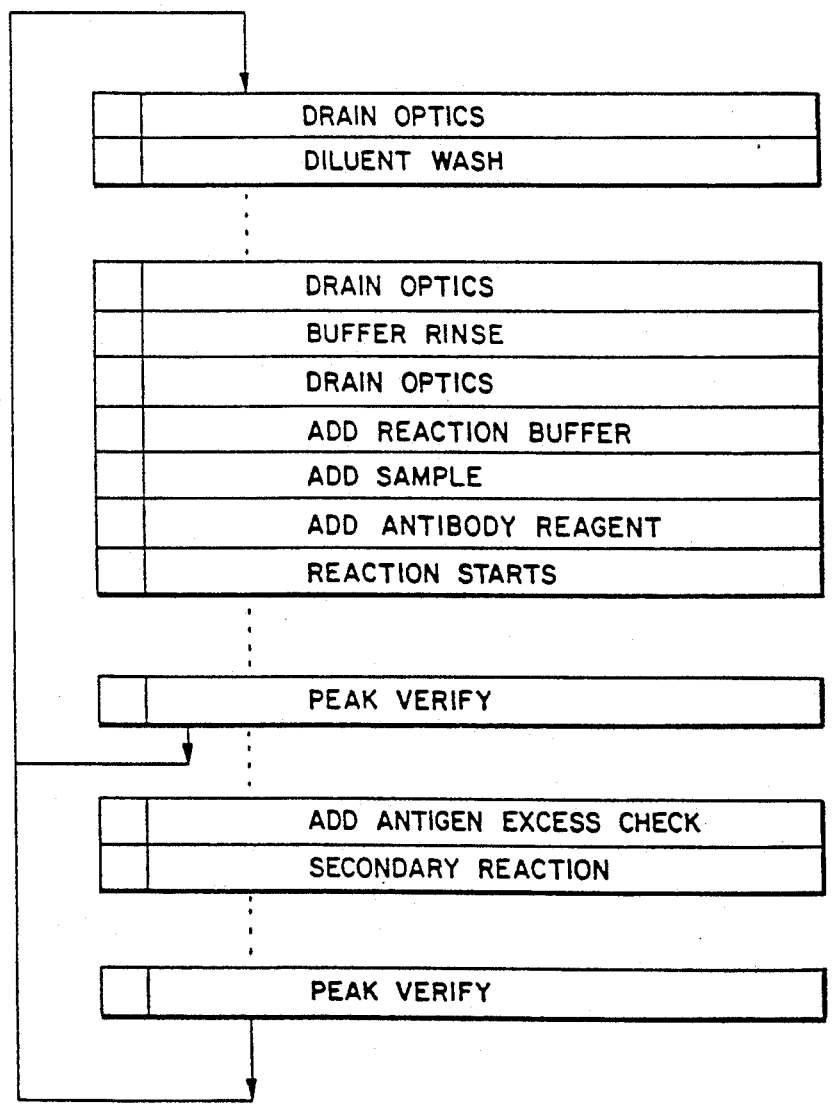

FIGS. 8A and 8B summarize the steps for operating system 16 of FIG. 1. First optics module 44 or 26 is drained and then filled with a diluent wash. The selected optics module is then drained and a buffer rinse solution is placed therein. The buffer rinse solution is then drained from the optics module. A reaction buffer is added to optics modules 24 and 26 and then the sample is injected therein. The antibody reagent is injected into optics module, and the antibody-antigen reaction begins.

Referring to FIG. 8B, the primary sample dilution sequence begins when sample probe 22 picks up sample from cell 134A. Sample diluter/dispenser 28 aspirates the diluent, and transport mechanism 20 moves sample probe 22 to cell 134B to dispense and mix the sample and diluent. The primary dilution sequence may be used to mix the sample and diluent in a ratio of 1:36, for example.

A secondary dilution sequence to mix the sample and diluent in a ratio of 1:216 begins when sample probe 22 picks up a selected volume of the diluted sample from cell 134B. Sample diluter/dispenser 28 agains aspirates the diluent, and transport mechanism 20 moves sample probe 22 to cell 134C to dispense and mix the sample and diluent therein. Sample probe 22 is then washed before picking up another sample.

The peak reaction rate is measured and verified using any suitable method. A preferred method for measuring and verifying the peak rate is described subsequently with reference to FIGS. 9-14. If no antigen excess check is to be done, then the above steps are repeated for a new sample. If an antigen excess check is to be done, then an antigen excess check reagent, or calibrator, is added to the sample in the optics module of interest. The antigen excess reaction, or secondary reaction proceeds, and its peak reaction rate is measured and verified. The process then repeats for a new sample if there is no antigen excess. If there was an antigen excess, the process is repeated for a more diluted sample of the antigen.

Referring to FIGS. 4-6, sample probe transport mechanism 20 includes a sample probe carriage 140 slidably mounted on a pair of rails 142 and 144. A stepper motor 146 drives a belt 148 that is connected to sample probe carriage mechanism 140, which supports sample probe 22 (not shown in FIG. 4). Stepper motor 146 preferably is capable of moving sample probe carriage 140 on rails 142 and 144 through a horizontal distance of about 15 inches at an average velocity of about 15 inches per second with a resolution of about 0.020 inch per motor step. Belt 148 is mounted on a roller (not shown) and a cog 152, shown in FIG. 5, that is connected to stepper motor 146 to be rotatably driven thereby. Cog 152 preferably has a plurality of teeth (not shown) thereon, and belt 148 preferably has a plurality of teeth (not shown) that engage the cog teeth to prevent slippage as stepper motor 146 drives cog 152 and belt 148.

Sample probe carriage 140 includes a second stepper motor 150 that moves a sample probe holder 154 vertically so that sample probe 22 may inserted into and withdrawn from cells 134A, 134B, etc. in sample turntable 18, nephelometric optics modules 44 and 46 and sample probe wash station 100. Stepper motor 150 preferably is capable of moving sample probe holder 154 through a vertical distance of about 2.0 inch at a velocity of about 4.0 inch per second with a resolution of about 0.15 inch per motor step.

Antibody probe transport mechanism 106 is similar to sample probe transport mechanism 20 and includes a stepper motor 156 that drives a belt 158 to which an antibody probe carriage 160 is mounted. Stepper motor 156 is substantially identical to stepper motor 146. Antibody probe carriage 160 is also slidably mounted on rails 142 and 144. Stepper motor 156 moves antibody probe carriage 160 horizontally in the same manner as stepper motor 146 moves sample probe carriage 140. Antibody probe carriage 160 includes a stepper motor 165 that moves an antibody probe holder 166 vertically so that it may inserted into and withdrawn from containers in antibody turntable 108, nephelometric optics modules 24 and 46 and antibody probe wash station 122.

Stepper motor 156 is substantially identical to stepper motor 150. Belt 158 is mounted on a roller 162 and a cog (not shown) that is substantially identical to cog 152 and connected to stepper motor 156 to be rotatably driven thereby. Belt 158 is preferably substantially identical to belt 148 and therefore preferably has a plurality of teeth thereon that engage corresponding teeth (not shown) on the cog mounted to stepper motor 156 to prevent slippage as stepper motor 156 drives cog 164 and belt 158. Roller 162 and cog 152 may be mounted upon a shaft 170 that extends from stepper motor 150. However, only cog 152 is driven by shaft 170 to drive belt 148. Roller 162 rolls freely upon shaft 170. The left hand end of belt 148 passes around a roller (not shown) that is mounted to stepper motor 156 like roller 162 is mounted to stepper motor 150. Thus each of belts 148 and 158 are driven by their corresponding stepper motors 146 and 156 and cog at one end, and the belts 148 and 158 pass around rollers at the ends that are not motor driven.

Referring to FIGS. 4 and 5, a radially slotted disk 172 is fixed to shaft 170 of stepper motor 146, and a radially slotted disk 174 is fixed to a shaft 176 extending from stepper motor 156. As best shown in FIG. 5, an infrared light source 178 directs a beam of light toward disk 172, which interrupts the beam as the shaft 170 and disk 172 rotate. Interruptions of the light beam trigger signals in a photodetector 180 mounted adjacent disk 172 on the side opposite from light source 178. Successive interruptions of the light beam produce signals indicative of whether shaft 170 is rotating. Radially slotted disk 172, shaft 170 light source 178 and photodetector 180 comprise a stall sensor 181. In a preferred embodiment, the light beam is interrupted once in every ten steps of stepper motor 146 to indicate proper operation thereof. The signals from photodetector 180 are received by a motor controller 182, shown in FIG. 2.

Since the radius of shaft 170 is known, rotation of disk 172 may be used to indicate the displacement of sample carriage 140 from a reference point 184. The product of the angular displacement in radians and the radius of shaft 170 is the distance of sample carriage 140 from reference point 184.

Figure 2:
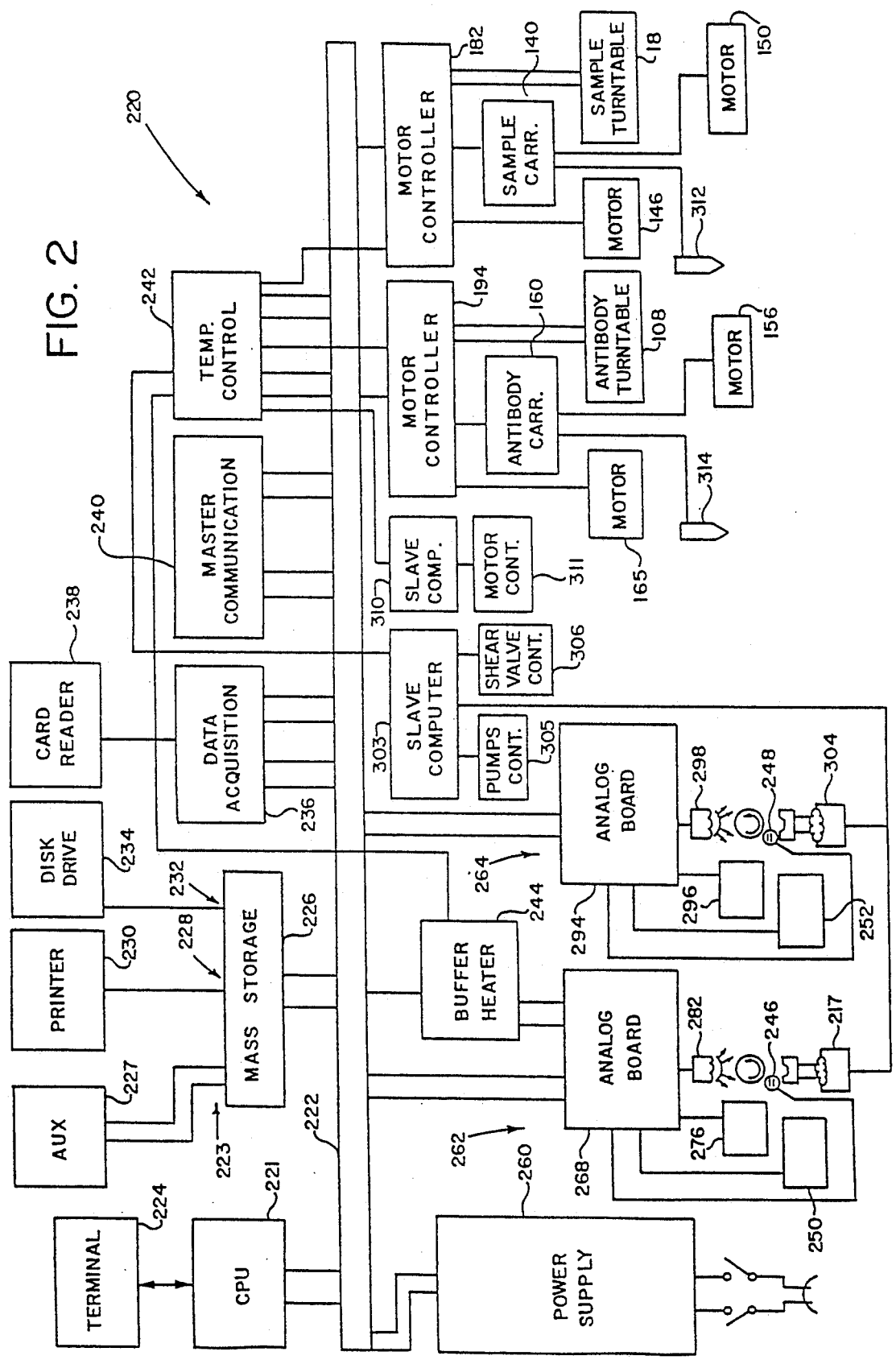
FIG. 2 is a block diagram of the electrical circuitry of the analyzer of FIG. 1.

Similarly, interruptions of a light beam by rotation of disk 174 provide signals to a motor controller 194, also shown in FIG. 2, to indicate whether stepper motor 156 is operating properly. These signals may also be used to determine the position of antibody probe carriage 160 from a reference point 188 near stepper motor 156.

Still referring to FIGS. 4 and 5, a light source 190 mounted to sample probe carriage 140 directs a beam of light upon a photodetector 196 to indicate when sample probe carriage 140 is at reference point 184. Upon reception of the beam from light source 190, photodetector 196 sends a signal to motor controller 182 to indicate that sample probe carriage 140 is at reference point 184. Similar apparatus (not shown) sends a signal to motor controller 194 to indicate when antibody probe carriage 160 is at reference point 188.

Sample probe carriage 140 and antibody probe carriage 160 are substantially identical; therefore only sample probe carriage 140 is described in detail herein. Referring to FIG. 4–6, sample prove carriage 140 includes a base 197 attached to belt 148 at a point 198 for movement along rails 142 and 144. Sample probe holder 154 includes an upright frame 199 slidably mounted to base 197, and an arm 200 preferably extends horizontally from frame 199. Frame 199 is fixed to a belt 202 at a point 201. Belt 202 passes around a roller 203 mounted to base 197 and a cog 204 fixed to stepper motor 150 to be rotatably driven thereby.

Actuation of stepper motor 150 moves sample probe holder 154 relative to base 197. A spring 205 may be connected between frame 199 and base 197 to bias the sample probe holder 154 in a predetermined direction. As shown in FIG. 6, spring 205 tends to pull sample probe holder 154 upward. A photodetector 206 and a light source 207 are mounted to base 197. Upon interruption of the beam by a projection 208 mounted to frame 199, photodetector 206 sends a signal to motor controller 182 to indicate that sample probe 22 is in an elevated position.

Nephelometric optics modules 44 and 46 are substantially identical; therefore only nephelometric optics module 44 is described in detail herein. Referring to FIG. 3A, nephelometric optics module 44 includes a lamp and lens housing 209 in which a lamp 210 and a lens system 211 are mounted. Lens system 211 collimates light from lamp 210, which may be an incandescent light source and directs the light to a filter 211a. Filter 211a is positioned between lens system 211 and reaction cuvette 48 to establish an excitation wavelength band for light that will impinge upon the sample therein. Light scattered at a forward angle of 70° is collected by a lens 212 and then passed through a filter 213 for isolating the wavelength band to be measured. The light that passes through filter 213 impinges upon a photodetector 214, which preferably is a silicon light detecting device. Light that travels essentially straight through reaction cuvette 48 is reflected from a mirror 215 and then directed out of the module.

Referring to FIG. 3B, optics module 44 includes a stirrer 216 for stirring the material in cuvette 48. A motor 217 actuates the stirrer 216.

Still referring to FIG. 3B, optics module 44 preferably includes a heat pump device 218 for selectively heating and cooling cuvette 48. A sensor 219 produces signals indicative of the temperature of cuvette 48 and heat pump device 218 is activated to maintain the temperature of cuvette within a specified range. Heat pump device 218 is preferably a Peltier effect device. The Peltier effect is a well known solid state phenomenon. When a current flows across a junction of two dissimilar conductors, heat (unrelated to normal ohmic heating effects) is absorbed or liberated depending upon the direction of current flow.

B. Electronic System

Referring to FIG. 2, analyzer system 16 includes an electronic control system 220 having four basic sections:

1. Main host computer section;
2. Slave computers for controlling motion;
3. Optics electronics; and
4. Power supply.

The main host computer section includes a central processing unit (CPU) 221 connected between a bus 222 and a terminal 224 that an operator uses to input information to CPU 221. CPU preferably includes a Z8001 microprocessor running at 5 MHz. A mass storage unit 226 connected to bus 222 preferably includes a pair of RS 232 ports 223 for connecting control system 220 to auxiliary devices 227. Mass storage unit 226 also preferably includes a parallel port 228 connected to a printer 230 and a disk control port 232 connected to a disk drive 234. Printer 230 may be any printer suitable for connection to a standard parallel port. Hewlett-Packard sells a suitable printer under the trademark HP-THINK JET. Disk control port 232 preferably includes an interface for a 3.5 inch floppy disk drive which has the purpose of loading software and data into CPU 221. Disk drive 234 should be compatible with a 3.5 inch floppy disk having at least 350 k bytes and preferably 720 k bytes of storage capacity.

A data acquisition unit 236 is connected between a card reader 238 and bus 222. Data acquisition unit 236 includes an analog to digital converter (not shown), a card reader interface unit (not shown) and optics control circuitry (not shown). Data acquisition unit 236 converts voltage readings coming to it from several different sources to digital signals for input to CPU 221. The optics control unit controls the gain, offset and signal cutoff of the nephelometric optics modules 44 and 46.

A master communication protocol unit 240 is connected to bus 222 for handling all communication functions dealing with the slave computers, which are described below.

A temperature control circuit 242 is connected to bus 222 and to a heater circuit 244 for providing control of the temperature of temperature controller 98 and optics modules 44 and 46. Temperature control circuit 242 handles all aspects of temperature control except for conversion of temperature to a corresponding voltage. Temperature control circuit 242 controls which of a pair of temperature sensors 246 and 248 data acquisition unit 236 will read. Temperature sensors 246 and 248 are preferably thermistors placed adjacent nephelometric optics modules 44 and 46 for sensing the temperatures of fluids supplied thereto.

Temperature controller block 98 preferably includes a pair of Peltier effect devices 250 and 252, which heat or cool the liquids passed therethrough to control the temperature liquids going into nephelometric optics modules 44 and 46. Temperature control is preferably provided to maintain the temperature of the optics modules 44 and 46 and reagents placed therein to 26.7°±0.5° C.

The degree of temperature control provided by the system 16 assures accuracy when the instrument is operating at ambient temperatures ranging between 18° C. and 35° C. The precise, long term temperature control provided by the present invention contributes to the ability of the system 16 to operate for about two weeks without requiring recalibration. This is a significant improvement over previous systems, which require daily calibration to provide satisfactory results.

Power is supplied to control system 220 from a power converter 260. Power converter 260 preferably provides regulated DC and 60 Hz AC power.

Control system 220 also preferably includes a pair of circuits 262 and 264 connected to bus 222 for connecting nephelometric optics modules 44 and 46 thereto. Circuit 262 includes an analog/optics interface unit 268 that is connected to a sensor preamplifier 276, Peltier effect device 250, thermistor 246 and a light source 282.

Circuit 264 includes an analog/optics interface unit 294 that is connected to a sensor preamplifier 296, Peltier effect device 252, thermistor 248, a light source 298.

A slave computer 303 is connected to bus 222 and to master communications board 240. Slave computer 303 controls stirrer motor 217 in nephelometric optics module 44 and a stirrer motor 304 in nephelometric optics module 46. Slave computer 303 is connected to a pump controller 305 that controls optics fill pump 60, optics drain pump 124, wash station drain pump 58 and antibody probe wash pump 124. A shear valve controller 306 is connected to slave computer 303 for controlling shear valves 28, 74 and 78.

A slave computer 310 is connected to a motor controller 311 that controls a stepper motor (not shown) for actuating pinch valve 52 to regulate the flow of buffer and diluent to sample diluter/dispenser 28 and to antibody/buffer dispenser 62. Slave computer 310 also provides control of stepper motors 40 and 84 for diluter/dispensers 28 and 80, respectively.

Motor controller 182 comprises a slave computer connected to bus 222 and to master communications board 240 for controlling sample transport mechanism 20. Motor controller 194 is similar to motor controller 182 and comprises a slave computer connected to bus 122 and to master communications board 240 for controlling antibody probe transport mechanism 106.

Motor controller 182 is connected to sample probe carriage 140 and stepper motor 146 for controlling operation thereof. Motor controller 182 is also connected to stepper motor 150 and to a fluid sense probe 312. Fluid sense probe 312 may be any device suitable for detecting when the sample probe 22 is lowered into a fluid. Motor controller 182 controls stepper motor 24 to control the angular position of sample turntable 18.

Motor controller 194 is connected to sample probe carriage 160 and stepper motor 156 for controlling operation thereof. Motor controller 194 is also connected to stepper motor 165 and to a fluid sense probe 314. Motor controller 186 controls stepper motor 109 to control the angular orientation of antibody turntable 108.

Each slave computer is preferably fast enough to handle two stepper motors running simultaneously at about 1000 pulses per second. Therefore, each slave computer may include an 8032 microprocessor running at 12 MHz and three 16 bit wide programmable counter timers. The execution rate of the bus should not be slower than one wait state per bus transaction. The system should have at least 512 k bytes of random access memory (RAM), 16 k bytes of programmable read only memory (PROM) and 16 k bytes of battery powered backup RAM.

Normalization of nephelometric optics modules 44 and 46 minimizes measurement differences. The two nephelometric optics are calibrated and normalized with an optical scatter standard (not shown), and rate signals are normalized with a rate normalization reagent.

Timing of Kinetic Nephelometric Measurements

There are many processes that may be used to operate the apparatus of the FIGS. 1-7. One exemplary preferred method is described in detail herein.

Figure 9:
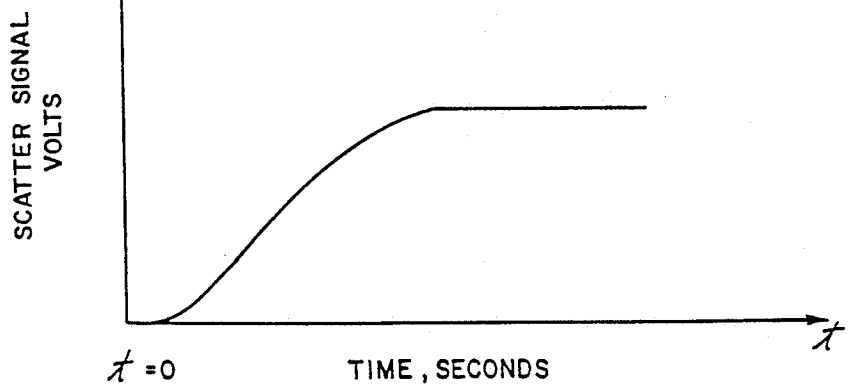
FIG. 9 graphically illustrates a typical scatter signal obtained from immunonephelometric analysis.

Referring to FIG. 9, a scatter signal starts at the origin of the graph when a diluted sample of an antigen and a specific amount of an antibody are injected into a reaction cuvette. The amount of light scattered from the precipitate formed by reaction of the antibody and antigen varies with time. The scatter signal will in general, be measured in volts, with one volt corresponding to an arbitrary number of scatter units. In a preferred embodiment of the invention, 1 volt of the scatter signal corresponds to 100 scatter units. The scatter signal starts at zero and increases to a maximum value as shown in FIG. 9.

Figure 10:
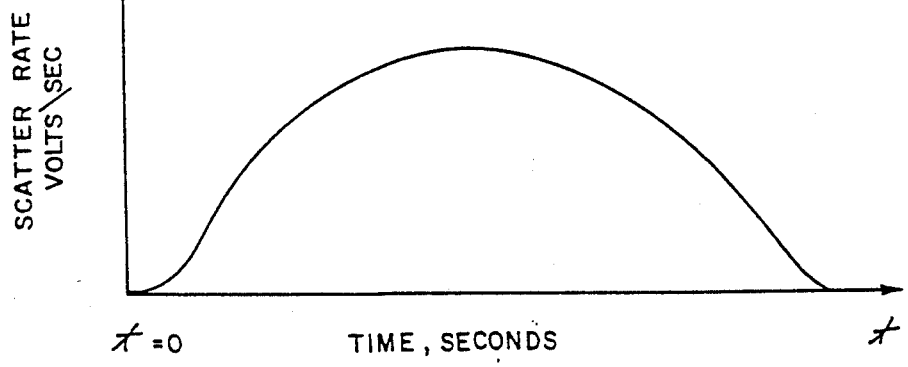
FIG. 10 graphically illustrates a typical rate signal.

Rate nephelometry is concerned with the derivative of the scatter signal with respect to time. FIG. 10 graphically illustrates a rate signal. The rate starts at zero and then increases rapidly to its peak value and then decreases. The desired rate to be measured in rate nephelometry is the peak rate. The peak rate occurs at the point of steepest slope on the scatter signal curve of FIG. 9. The peak rate is the maximum value attained by the curve of FIG. 10. Since the rate rises from zero to the peak value and then decreases, the slope of the rate curve is zero at the peak rate.

Referring to FIG. 10, after the peak rate is attained, the rate signal may be monitored for a peak rate verification time to assure that the highest value of the rate measured is actually the peak rate for the reaction. After verification of the peak rate, a calibrator for antigen excess checking is injected into the reaction cuvette, and the rate signal is zeroed. The calibrator includes additional antigen. If the reaction already was in antigen excess, the rate will not change appreciably as the calibrator is added to the cuvette. If the reaction had been in antibody excess, then addition of the calibrator causes the rate to increase to a value much larger than its prior value. The rate obtained prior to addition of the calibrator is not the desired measurement if the rate increases above a predetermined value after addition of the calibrator.

The reaction is terminated if the rate exceeds a threshold value after injection of the calibrator. Termination of the reaction after determining that the measured rate was obtained under the desired conditions saves several seconds in the time required to complete the analysis of the sample.

Figure 11:
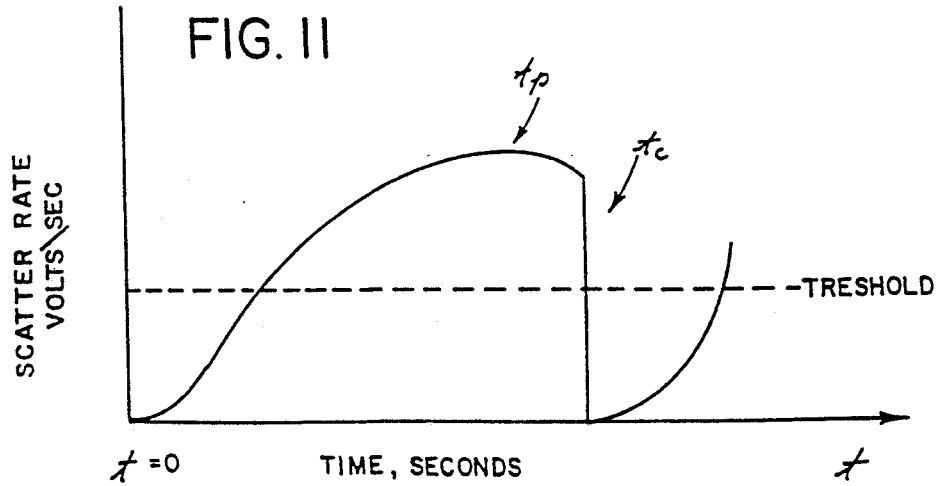
FIG. 11 illustrates a rate for an antigen-antibody reaction that began with an excess of antibody.

FIG. 11 represents the rate for a system that started in antibody excess. The antibody and sample are injected at time $t=0$. The peak rate of the reaction occurs at a time $t_p$, and the reaction continues for a peak verify time before injection of the calibrator containing additional antibody. After the peak verify time, the rate signal is set to zero, and the calibrator is injected at a time $t_c$. The rate of reaction after injection of the calibrator exceeds a threshold value, which means the sample has an excess of antibody. Analysis of experimental data for IgG has shown that if the rate after injection of the calibrator exceeds 300 rate units, the system was not in antigen excess when the previous peak rate was measured. If the rate after injection of the calibrator exceeds the threshold, then the rate measurement is accepted as being valid. The threshold depends upon the test being performed.

Figure 13A:
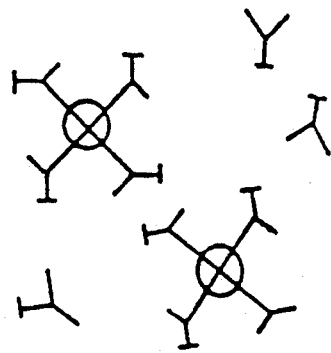
FIG. 13A represents a molecular complex formed by reaction of a typical antibody and its antigen under an antibody excess condition.
Figure 13B:
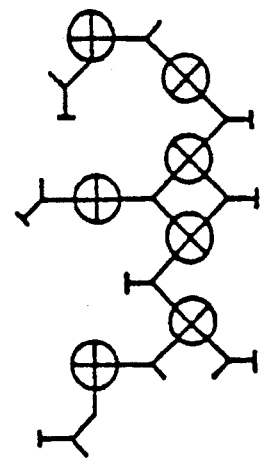
FIG. 13B represents a molecular complex formed by reaction of a typical antibody and its antigen when the antibody and antigen have nearly equivalent concentrations.
Figure 13C:
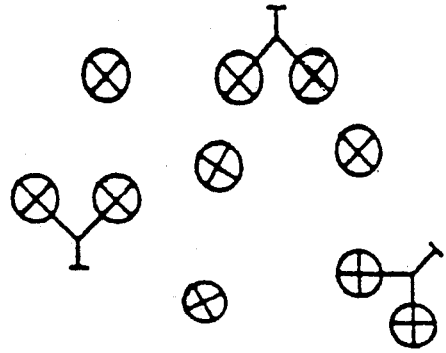
FIG. 13C represents a molecular complex formed by reaction of a typical antibody and its antigen under an antigen excess condition.

Referring to FIG. 13A, a low rate will occur when the sample has an excess of antibody, where there is little precipitate formed. The circles with the crossed lines therein represent antigen molecules, and the Y-shaped figures represent antibody molecules. FIG. 13B represents near equivalence of the antibody and antigen, which forms a large amount of precipitate represented by the large number of interconnections between the antigen and antibody molecules. FIG. 13C represents the condition of antigen excess.

Figure 12:
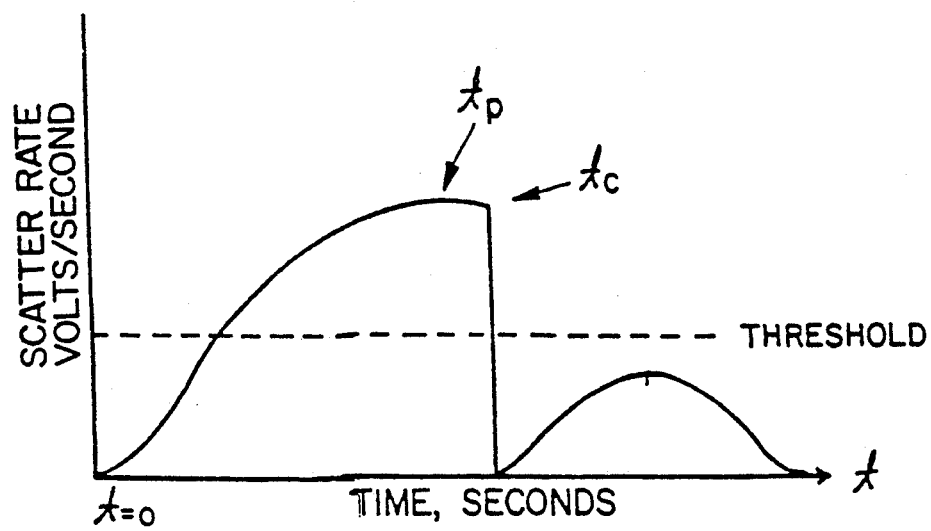
FIG. 12 illustrates a rate for an antigen-antibody reaction that began with an excess of antigen.

A low scatter signal may represent either a low antigen concentration in the sample or an antigen excess condition. Therefore, it is necessary to test each verified peak rate to determine whether it corresponds to antigen excess or antibody excess. FIG. 12 illustrates the method of the invention when the reaction is in antigen excess. The antibody and sample are injected at time $t=0$. The peak rate of the reaction occurs at a time $t_p$, and the reaction continues for a peak verify time before injection of the calibrator containing additional antigen. After the peak verify time, the scatter signal is set to zero, and the calibrator is injected at a time $t_c$.

The rate of reaction represented is less than the threshold value, which means that the sample has an excess of antigen. If the rate after injection of the calibrator is less than the threshold, the rate is monitored until it is ascertained that the rate will not exceed the threshold. If the rate after injection of the calibrator remains less than the threshold, then subsequent scatter measurements are made with the same diluted to obtain a measurable rate.

The first primary rate measurements may be made with 42 $\mu l$ antigen diluted 1:36. The second primary measurement is typically made with a sample comprising antigen and diluent in the ratio of 1:216. If the second sample is in antigen excess, then a third measurement is made with 7 $\mu l$ of the antigen diluted a 1:216 ratio, which has one sixth of the amount of antigen as the second sample.

Analysis of experimental data has also shown that as the rate increases, the time required to verify the peak decreases. A reaction with a high rate gives a high signal to noise ratio. The curve is relatively smooth so noise spikes rarely cause a measured maximum rate to be erroneous. As the peak rate decreases, the time required to reach the peak rate increases, and the scatter signal decreases, which increases the possibility that a noise spike generated from interfering elements such as air bubbles and dust particles will generate a false indication of the peak rate. The peak verify time should have sufficient duration to average the signal to determine whether an indicated peak is an actual peak rate or a noise spike in the curve.

In a preferred embodiment, the system is capable of measuring a wide range of antigen concentrations of 250 to 3600 mg/dl in the sample. For example, the system is capable of measuring IgG concentrations of 250 to 3600 mg/dl in the sample. The scatter signal increases in magnitude as the antigen concentration increases. For high rates, corresponding to an antigen concentration of 3600 mg/dl for example, the peak verify time may be as short as five seconds. Low rates may require peak verification times about sixteen seconds.

To take advantage of the relation between the scatter intensity and the time required to verify the peak rate, the invention includes adjustment of the peak verify time of a specified rate of scatter intensity range. The adjustment of the peak verify time may be expressed in terms of the following equation:

$$TPV = TPV_{max} - [(TPV_{max} - TPV_{min}) \times (\text{Int. rate})/\text{range}],$$

where
Int. rate = measured peak rate − minimum allowable rate;
range = maximum allowable rate − minimum allowable rate;
$TPV_{max}$ = maximum allowable time for any rate measurement; and
$TPV_{min}$ = minimum allowable time for any rate measurement.

From inspection of the equation it is seen that the peak verify time is continuously varied as the measured peak rate varies. The peak verify time may be described by a ramp function that increases linearly as the measured rate increases. Therefore, the adjustment of the peak verify time according to the invention is called "ramping".

The times $TPV_{max}$ and $TPV_{min}$ are determined through trial observations of the reaction to be analyzed. The minimum time should be of sufficient duration to verify the rate for a relatively fast reaction. The maximum time is used in analyzing slow reactions and should be of sufficient duration to assure that a measured peak rate is the actual peak. For analysis of fast reactions $TPV_{min}$ is about 5 seconds for all antigen-antibody reactions. $TPV_{max}$ varies with the chemistry and ranges from about 10 seconds for haptoglobin to about 45 seconds for alpha acid glycoprotein. The minimum and maximum allowable rates also depend on the chemistry and range from about 150 rate units to 500 rate units for typical reactions.

After it is determined that an antigen excess check is required, the scatter signal is mathematically set to zero, which reduces the first derivative rate to zero at the end of the peak verify period. This zeroing process allows the analysis to proceed at the full speed of the chemical reaction without unnecessary delays. The antigen excess check can be monitored following injection of the calibrator having a known analyte concentration.

Referring to FIGS. 14A-14J, all chemistry evaluation algorithms are run as real time processes, with allows the system run the same code as two different processes. To evaluate the chemical reactions on the two different optics modules, the chemical analysis algorithms are run as two different processes. A variable is passed to the the process when it is created to indicate which optics module the the process is to analyze. These processes are given the same priority so that each receives equal CPY time.

The chemical analysis module analyzes data output from an interrupt service routine ISR. The ISR that performs the data acquisition and the digital filtering operations (the clock ISR) is controlled by a counter-timer integrated circuit that produces a pulse every 10 ms. A suitable counter-timer is an Intel 8253 integrated circuit. Each clock ISR evaluates a different optics module on every pulse. Therefore, a data point is taken every 20 ms from each optics module. The clock ISR also updates timers used in the chemical analysis process as explained subsequently.

Figure 14A:
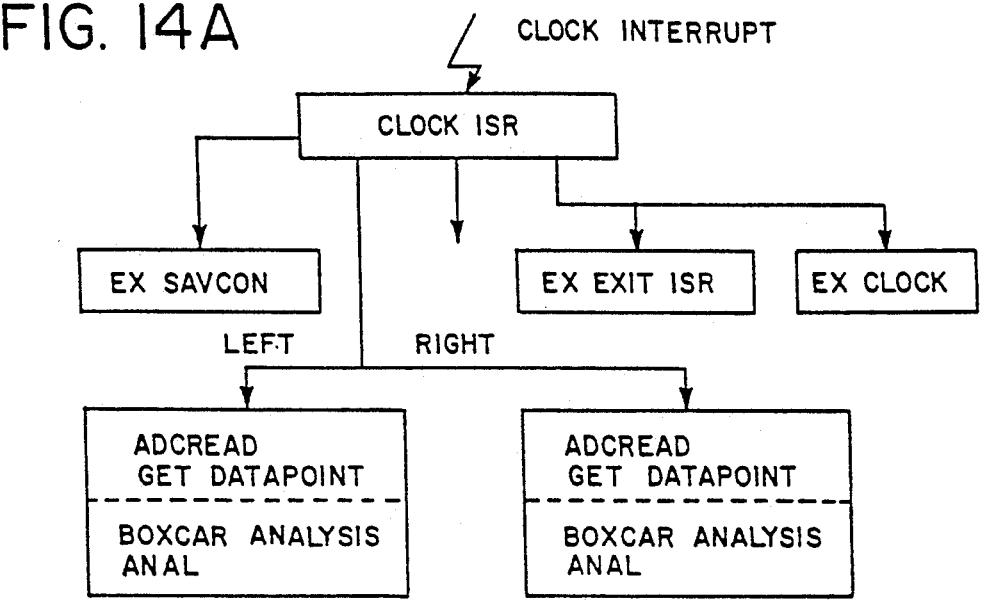
FIGS. 14A-14J are flow charts of algorithms that may be used with the apparatus of FIGS. 1-7.

Referring to FIG. 14A, a routine GET DATAPOINT is called from every clock ISR. The GET DATAPOINT routine determines which optics module 44 or 26 is to be evaluated and enables the corresponding channel of a multiplexer (not shown). A routine ADCREAD reads the data from the optics modules 24 and 26. The ADCREAD routine reads the data via the microprocessor chip and manages the settling and conversion times. The data indicative of the scatter signal is stored in a variable RAWSCATL for the left optics module and in a variable RAWSCATR for the right optics module.

After calling the GET DATAPOINT routine, the clock ISR calls a routine ANAL within the same time slice to ensure analysis of a new data point by the ANAL routine. The ANAL routine controls both the signal processing and digital filtering routines. The ANAL routine processes the data by subtracting a baseline reading BASEADC therefrom and dividing by the sensitivity factor after multiplying by 10,000. The sensitivity factor is determined by the gain setting. The processed data reading is then sent to a digital filtering routine called BOXCAR.

Figure 14B:
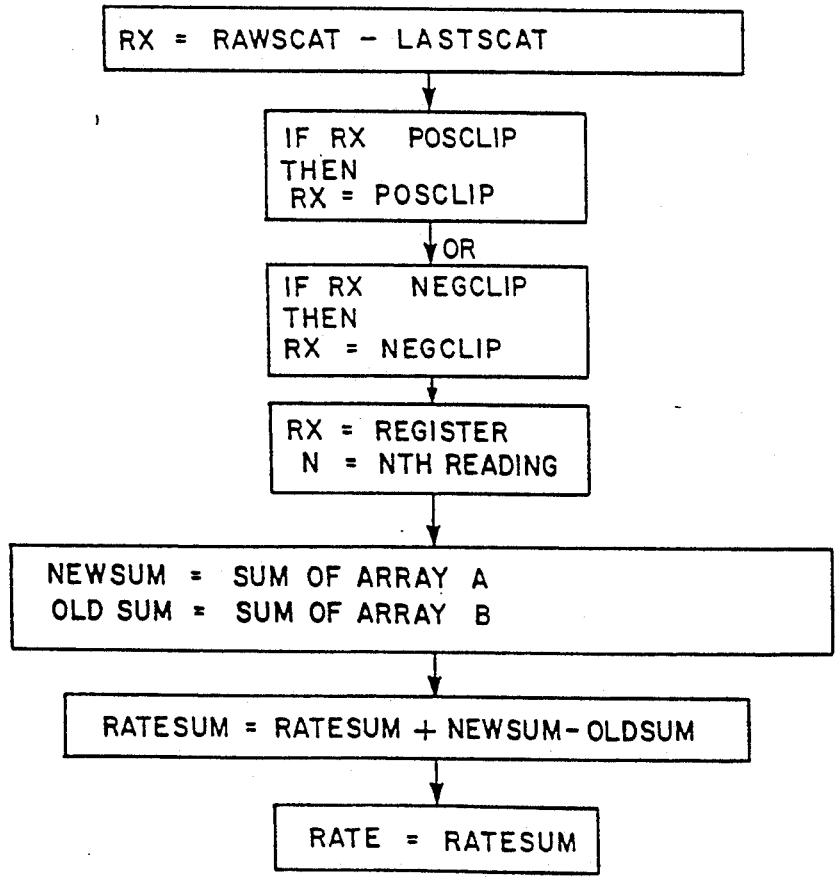

Referring to FIG. 14B, BOXCAR is a second order digital filtering mechanism to smooth the curve created by the integration of differences created by consecutive scatter or ADC readings over a finite time period. BOXCAR subtracts the current rawscatter from the last scatter reading LASTSCAT and stored in register X (RX). If the difference obtained from the preceding step is greater than the value of POSCLIP or less than the value of NEGCLIP, it is set to the limiting value. The first derivative data stored in RX is then fed into the digital filter. The digital filter comprises two arrays that each may include up to 200 data points. Data points are fed into BOXCAR from the beginning of a first array A. When array A becomes full, data points are then fed into a second array B. Rate units are calculated by subtracting the sum of array A from the sum of array B and summing the subtractand with all previous subtractands.

Figure 14C:
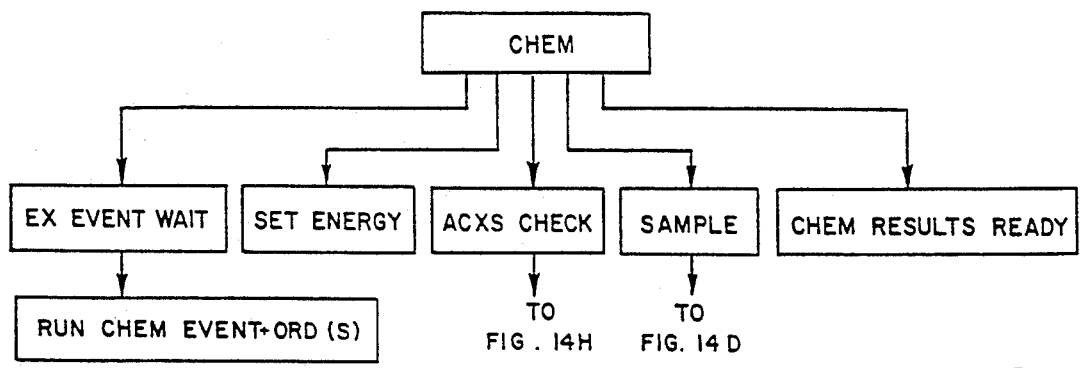

Referring to FIG. 14C, the chemical analysis process verifies peak rate values and calculates the concentration of a sample from the peak rate. The chemical analysis process also monitors both chemistry timing requirements and irregular testing conditions. In order to service the chemical reaction properly and communicate with the rest of the system, the chemical analysis process interacts closely with a scheduling process.

When the chemical analysis process is created, a parameter (s) indicating which optics module is to be evaluated is passed to the process. This parameter then passes to a CHEM routine. The CHEM routine then waits until the scheduler signals it to reactivate. The wait is performed by calling a command EX EVENT WAIT on the RUN CHEM EVENT. The scheduler will activate the CHEM routine by calling a command EX EVENT SET on the RUN CHEM EVENT.

After CHEM is reactivated, it can perform three different actions. These three actions are determined by the variable RXNTYPE, which indicates either an energy set, a primary reaction analysis, or a secondary reaction analysis should be performed. If an energy set is to be performed, then a routine SET ENERGY is called. If a primary reaction is to be performed, then a routine SAMPLE is called. Likewise for a secondary reaction, a routine AGXS CHECK is called.

Figure 14D:
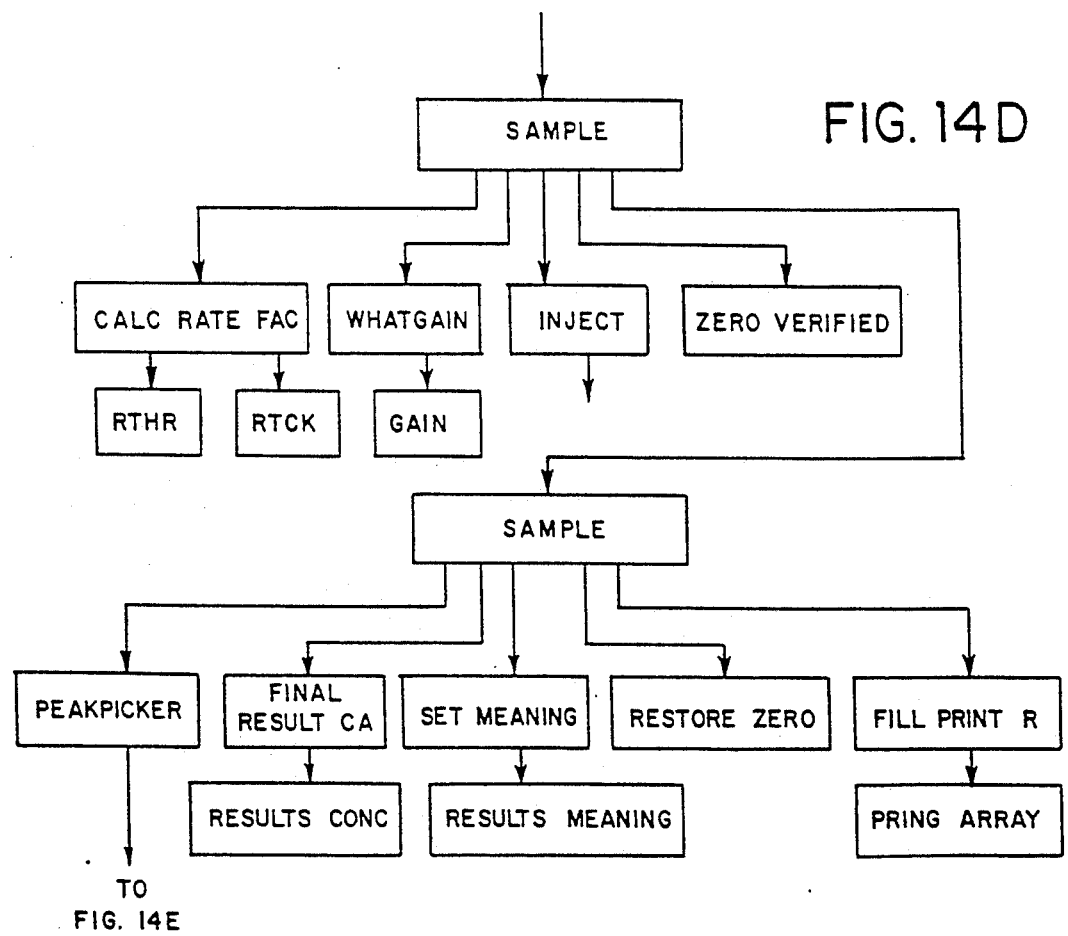

Referring to FIG. 14D, the SAMPLE routine evaluates all primary reactions, including all chemistries for both calibrations and sample tests. The sample has already been injected when the scheduler reactivates the chemical analysis process to evaluate a primary reaction. The SAMPLE routine then begins analysis of the sample. The steps of the SAMPLE routine occur chronologically in the order described below.

First the gain is set at the WHATGAIN step, and then at the INJECT step the scatter signal is set to zero and the digital filter is cleared. At the ZERO VERIFIED step, a signal is sent to the scheduler to indicate that the antibody may be injected.

Figure 14E:
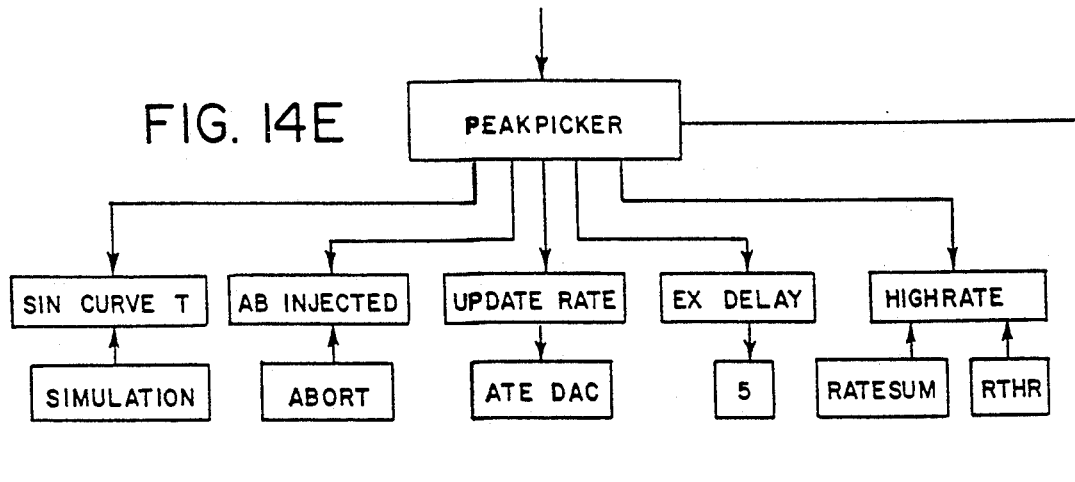
Figure 14F:
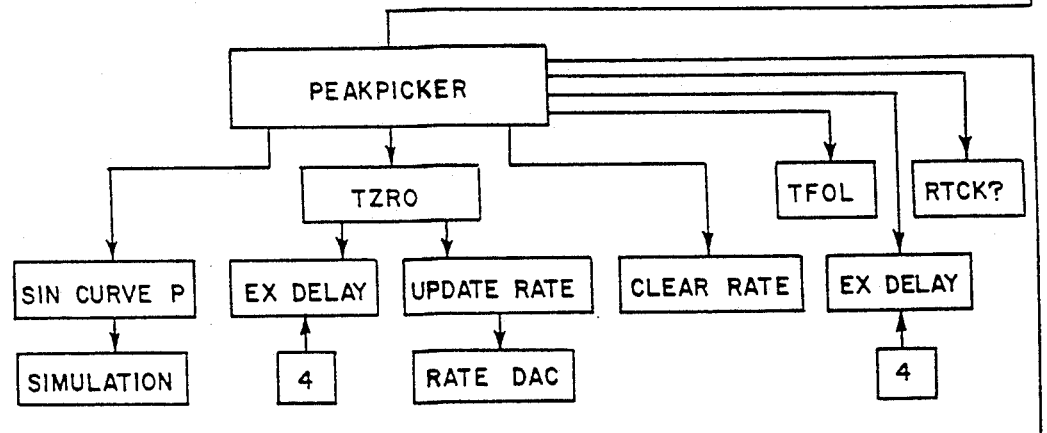
Figure 14F:
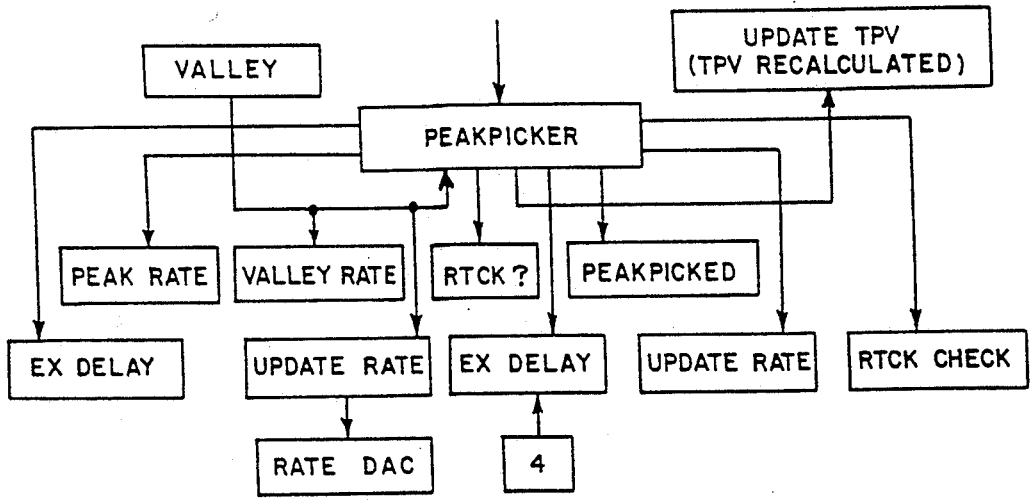
Figure 14G:
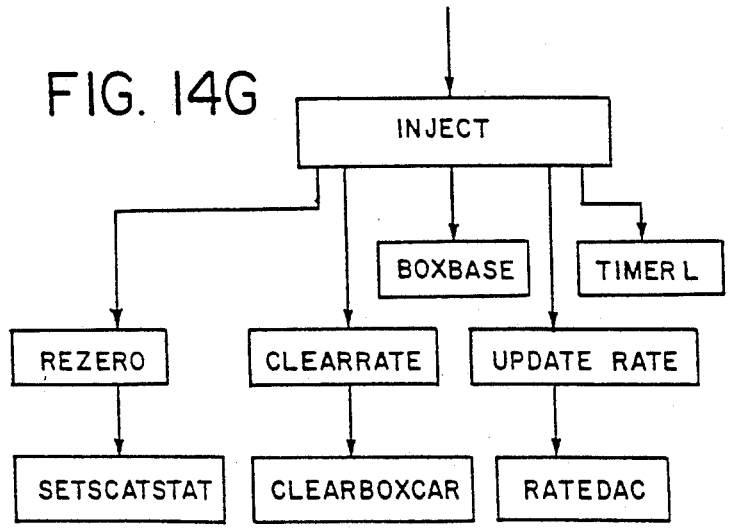
Figure 14H:
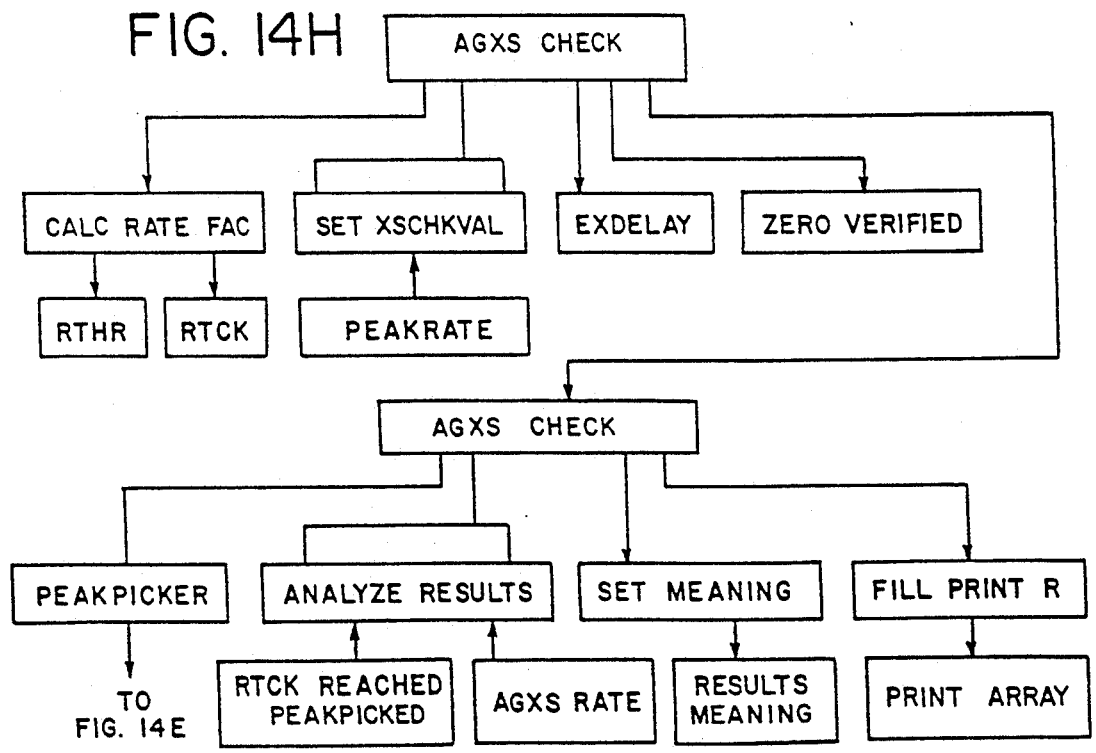
Figure 14:
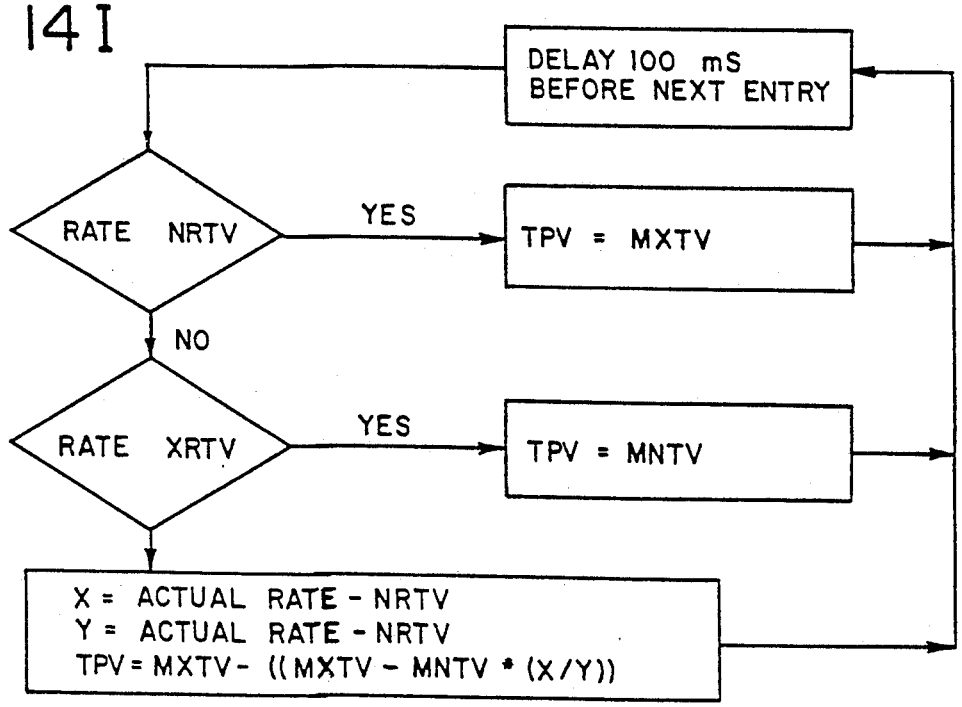
Figure 14:
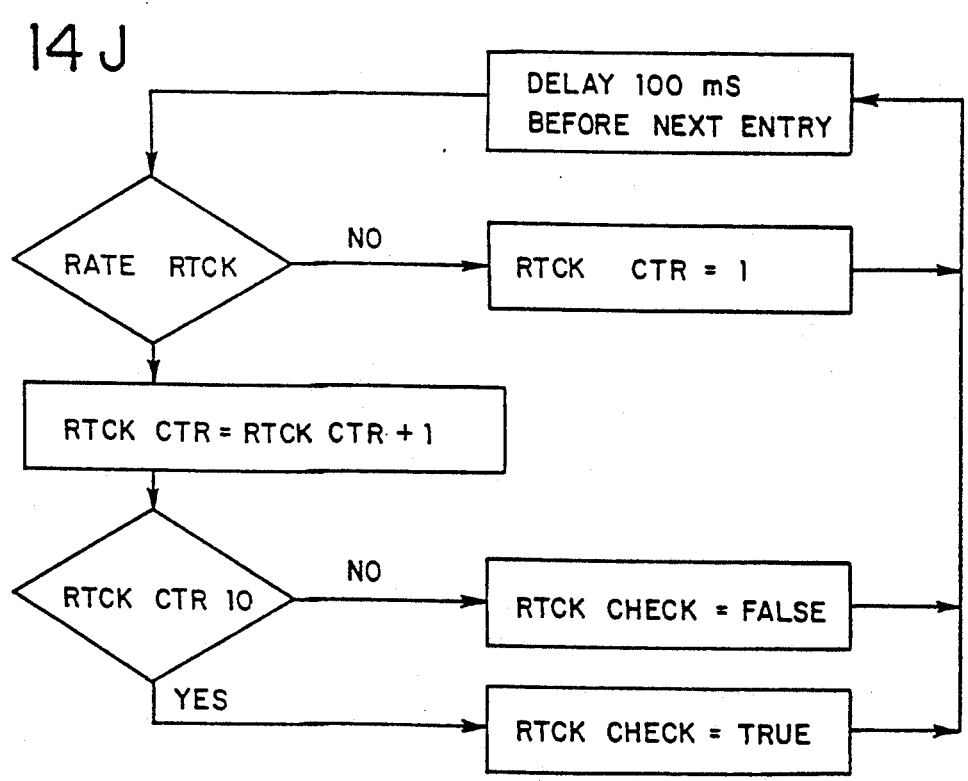

A PEAKPICKER routine, shown in FIGS. 14E and 14F, waits for injection of the antibody, which is signaled by the scheduler by setting the variable AB INJECTED. If, at any time before the antibody is injected, the rate goes above a predetermined RTHR value, then the injection is delayed. If the antibody is not injected within 20 second, then the scheduler aborts the test.

During a TZRO step of the PEAKPICKER routine, the timer is set to a time period designated by a TZRO card parameter. At the end of this period the digital filter is cleared or reset. During a TFOL step the PEAKPICKER routine sets the timer to a time period designated by a TFOL time parameter minus the TZRO card parameter. This step provides a delay for entry into the next step. If the system is performing an antigen excess check, the rate is compared against a value RTCK. If the RTCK is reached during an antigen excess check, then the analysis of the reaction is terminated.

The PEAKPICKER routine also includes a VALLEY step, shown in FIG. 14F, that monitors the reaction rate. The VALLEY step requires that the chemistry must have an increasing rate for a designated time, which is three seconds in a preferred embodiment of the invention. If the system is performing an antigen excess check, the rate is compared to the value of RTCK; and if the rate attains the RTCK value during the antigen excess check, then analysis of the reaction is terminated.

The PEAKPICKER routine also includes a TPV section, shown in FIG. 14I, that requires that the rate not exceed the peak rate for the peak verify time. The peak verify time is recalculated by an UPDATE TPV routine at short time intervals of 100 ms in the preferred embodiment. The peak verify time is calculated by comparing the actual rate measured to a parameter NRTV, which is the minimum rate for verification of the peak, and to a parameter XRTV, which is the maximum rate for verification of the peak. If the actual rate is less than the NRTV, then the peak verify time is set to a parameter MXTV, which is the predetermined maximum time allowable for verifying the peak rate. If the actual rate exceeds the XRTV, then the peak verify time is set to a parameter MNTV, which is the predetermined minimum value for verifying the peak rate. If the actual rate is between the NRTV and the XRTV, then the peak verify time TPV is calculated as follows:

$$X = \text{actual rate} - NRTV$$

$$Y = XRTV - NRTV$$

$$TPV = MXTV - ((MXTV - MNTV) * (X/Y))$$

The BOXCAR routine terminates immediately after elapse of the peak verify time. If the system is performing an antigen excess check, the rate is compared to the value of RTCK; and if the rate attains the RTCK value during the antigen excess check, then analysis of the reaction is terminated.

After execution of the PEAKPICKER routine, the SAMPLE then enters a FINAL RESULT CALC routine in which the concentration of the antigen is computed. A SET MEANING routine interprets the results of the preceding step and then sends the results to the SCHEDULER routine. A RESTORE ZERO routine then sets the scatter signal to prereaction levels. A FILL PRINT RESULTS routine then enters the calculated results into a print array as the information to be used for printing the results of the analysis of the sample.

When the primary reaction is complete, the routine CHEM RESULTS READY is sent to the scheduler. The chemical analysis process then returns to the CHEM routine and waits to be reactivated by the scheduler. The scheduler then calls the routine AGXS NEEDED to determine whether a secondary reaction is required. If a secondary reaction is required, then the RXN TYPE is set to AGXS RUN and an EX EVENT SET on the RUN CHEM EVENT is called by the scheduler. The CHEM routine is reactivated, and the AGXS CHECK routine of FIG. 12H is called.

Before a second injection and the analysis of increasing rate can be performed, the rate must fall below the RTCK value. The RTCK ROUTINE is shown in FIG. 14J. After the rate is below the RTCK value, the second antibody injection is performed. The routine AGXS CHECK calls the PEAKPICKER routine, which analyzes the secondary reaction in the same manner as for the primary reaction. However, if the rate exceeds the rate check value RTCK, the rate analysis is aborted; and the reaction is determined not to be in antigen excess. If the rate does not climb above the rate check value, the reaction is determined to be in antigen excess. If a peak is not picked, the reaction is determined to be an unstable sample.

What is claimed is:

1. A system for analyzing a reaction between reagents, comprising:

a reaction cuvette for containing the reagents during the reaction;

first reagent delivery means for delivering a first reagent to said reaction cuvette;

second reagent delivery means for delivering a second reagent to said reaction cuvette;

means for sensing the temperature of the reaction cuvette with first temperature sensor means and including means for selectively heating or cooling the cuvette to maintain the temperature in a predetermined temperature range, the reaction cuvette being for containing the reagents during the reaction;

means for sensing the temperature of reagents with second temperature sensor means, the reagents being delivered by a reagent delivery means for injecting at least one reagent into the reaction cuvette, and means for selectively increasing or decreasing the temperature of the reagents independently of said cuvette to maintain the temperature of the reagent in a predetermined temperature range; and means for analyzing the reaction between the reagents by processing the light scattered from the reaction in the reaction cuvette.

2. The system of claim 1 wherein said temperature controlling means includes:

first temperature sensor means for sensing the temperature of said reaction cuvette;

first heat pumping means for selectively increasing or decreasing the temperature of said reaction cuvette; and means responsive to said first temperature sensor means for activating said first heat pumping means to maintain the temperature of said reaction cuvette within a selected temperature range.

3. The system of claim 2 wherein said temperature controlling means further includes:

second heat pumping means for selectively increasing or decreasing the temperatures of the reagents; and means responsive to said second temperature sensor means for activating said second heat pumping means to maintain the temperature of the first and second reagents within the selected temperature range.

4. The system of claim 1 wherein said temperature controlling means further includes:

heat pumping means for selectively increasing or decreasing the temperatures of first and second reagents; and means responsive to said temperature sensor means for activating said heat pumping means to maintain the temperature of the first and second reagents within a selected temperature range.

5. The system of claim 1 wherein said first and second temperature sensor means each comprises a thermistor means in thermal contact with the first and second reagents.

6. The system of claim 2 wherein said first heat pumping means comprises an electrically controlled heating and cooling device.

7. The system of claim 6 wherein said electrically controlled heating and cooling device is a Peltier effect device.

8. The system of claim 1 wherein the first reagent comprises an antigen and the second reagent comprises an antibody and said reaction cuvette is positioned within an nephelometer such that the reaction of the antigen and antibody may be monitored by processing light scattered from the reaction.

9. The system of claim 1 wherein said first reagent delivery means comprises:
a sample pick up station;
sample probe means for withdrawing a selected sample from said sample pick up station; and
sample transport means for carrying said sample probe from said sample pick up station to said reaction cuvette.

10. The system of claim 9 wherein said sample transport means comprises:
a rail;
a sample probe carriage slidably mounted on said rail;
first stepper motor means for controlling the position of said sample probe carriage along said rail; and
first position sensor means for sensing when said sample probe carriage is adjacent a first reference point fixed relative to said rail.

11. The system of claim 10 wherein said sample transport means further comprises stall sensor means for sensing operation of said first stepper motor.

12. The system of claim 10 wherein said sample transport means further comprises:
second stepper motor means mounted to said sample probe carriage for moving said sample probe means perpendicular to said rail, said sample probe means being movable between a retracted position for selectively establishing fluid communication with said sample station, said reaction cuvette and a sample probe wash station and an extended position for moving said sample probe means between said sample station, said reaction cuvette and said sample probe wash station; and
second position sensor means for sensing when said sample probe means is in said extended position.

13. The system of claim 1 wherein said second reagent delivery means comprises:
an antibody pick up station;
antibody probe means for withdrawing an antibody from said antibody pick up station; and
antibody transport means for carrying said antibody from said antibody pick up station to said reaction cuvette.

14. The system of claim 10 wherein said sample transport means comprises stall sensor means for sensing operation of a first stepper motor.

15. The system of claim 10 wherein said sample is an antibody and said antibody transport means comprises;
said rail;
an antibody probe carriage slidably mounted on said rail;
third stepper motor means for controlling the position of said antibody probe carriage along said rail; and
third position sensor means for sensing when said antibody probe carriage is adjacent a second reference point fixed relative to said rail.

16. The system of claim 15 wherein said antibody transport means further comprises;
fourth stepper motor means mounted to said antibody probe carriage for moving said antibody probe means perpendicular to said rail, said antibody probe means being movable between a retracted position for selectively establishing fluid communication with said antibody pickup station, said reaction cuvette and a antibody probe wash station and an extended position for moving said antibody probe means between said antibody station, said reaction cuvette and said antibody probe wash station; and
fourth position sensor means for sensing when said antibody probe means is in said extended position.

17. A system for analyzing a reaction between reagents in a nephelometer, comprising:
a reaction cuvette; means for sensing the temperature of the reaction cuvette with first temperature sensor means and selectively heating or cooling the cuvette to maintain the temperature in a predetermined temperature range;
means for sensing the temperature of reagents with second temperature sensor means, the reagents being delivered by a reagent delivery means for injecting at least one reagent into the reaction cuvette and selectively increasing or decreasing the temperature of the reagents independently of said cuvette to maintain the temperature of the reagents in a predetermined temperature range;
means for injecting an antigen reagent and an antibody reagent into the reaction cuvette for containing the reagents during the reaction wherein the means for injecting the reagent includes:
(a) means for aspirating a selected antigen reagent sample into a sample probe from a sample pick up station;
(b) means for automatically transporting said sample from said sample pick up station to said reaction cuvette;
(c) means for aspirating an antibody reagent from an antibody pick up station into an antibody probe means; and
(d) means for transporting the antibody from the antibody pick up station to said reaction cuvette; and
means for monitoring the reaction of the antigen and antibody by processing light scattered from the reaction in a nephelometer.

18. A system for analyzing a light scattering reaction between reagents in a nephelometer, comprising:
a reaction cuvette;
means for sensing the temperature of the reaction cuvette with first temperature sensor means;
means for sensing the temperature of reagents with second temperature sensor means, the reagents being delivered by a reagent delivery means for injecting reagents into the reaction cuvette;

means for selectively increasing or decreasing the temperatures of at least one of the reagents and the reaction cuvette independently of the other to maintain the temperature in a predetermined range;

means for combining different quantities of a diluent with a sample reagent and establishing different concentrations of sample reagent;

means for providing a range of different buffers and transferring a selected buffer to the reaction cuvette;

means for injecting selected reagents into the reaction cuvette; and means for analyzing the reaction between the reagents by processing the light scattered from the reaction in the reaction cuvette.

19. A system for analyzing a reaction between reagents in a nephelometer, comprising:

a reaction cuvette means for sensing the temperature of the reaction cuvette with first temperature sensor means and selectively heating or cooling the cuvette to maintain the temperature in a predetermined temperature range, the reaction cuvette being for containing the reagents during the reaction;

means for sensing the temperature of reagents with second temperature sensor means, the reagents being delivered by a reagent delivery means for injecting at least one reagent into the reaction cuvette, and selectively increasing or decreasing the temperature of the reagents independently of said cuvette to maintain the temperature in a predetermined temperature range;

means for combining different quantities of a diluent with a selected antigen reagent sample and establishing different concentrations of the sample;

means for providing a range of different reaction buffers and transferring a selected reaction buffer to the reaction cuvette via the reagent delivery means;

means for injecting an antigen reagent and an antibody reagent into the reaction cuvette, wherein the means for injecting the reagents include:
 (a) means for aspirating a selected concentration of the antigen reagent sample into a sample probe from a sample pick up station,
 (b) means for transporting said sample from said sample pick up station to said reaction cuvette,
 (c) means for aspirating an antibody reagent from an antibody pick up station into an antibody probe means, and
 (d) means for transporting the antibody from the antibody pick up station to said reaction cuvette; and means for monitoring the reaction of the antigen and antibody by processing light scattered from the reaction in the reaction cuvette.

20. A system for analyzing a light scattering reaction between reagents in a nephelometer, comprising:

a reaction cuvette; means for sensing the temperature of a reaction cuvette with first temperature sensor means;

means for sensing the temperature of reagents with second temperature sensor means, the reagents being delivered by a reagent delivery means for injecting at least one reagent to the reaction cuvette;

means for selectively increasing or decreasing the temperature independently of at least one of the reagents and reaction cuvette to maintain the temperature in a predetermined temperature range;

means for combining different quantities of a diluent with a sample reagent and establishing different concentrations of sample reagent;

means for injecting selected reagents into the reaction cuvette; and means for analyzing the reaction between the reagents by processing the light scattered from the reaction in the reaction cuvette.

21. A system for analyzing a reaction between reagents in a nephelometer comprising:

a reaction cuvette;

means for sensing the temperature of the reaction cuvette with first temperature sensor means and selectively heating or cooling the cuvette to maintain the temperature in a predetermined temperature range, the reaction cuvette being for containing reagents during the reaction;

means for sensing the temperature of reagents with second temperature sensor means, the reagents being delivered by a reagent delivery means for injecting at least one reagent into the reaction cuvette and selectively increasing or decreasing the temperature of the reagents independently of the cuvette to maintain the temperature in a predetermined temperature range;

means for combining different quantities of a diluent with a selected antigen reagent sample and establishing different concentrations of the sample;

means for injecting an antigen reagent and an antibody reagent into the reaction cuvette for containing the reagents during the reaction wherein means for injecting the reagent, includes:
 (a) means for aspirating a selected antigen reagent sample into a sample probe from a sample pick up station,
 (b) means for transporting said sample from said sample pick up station to said reaction cuvette,
 (c) means for aspirating an antibody reagent from an antibody pick up station into an antibody probe means, and
 (d) means for transporting the antibody from the antibody pick up station to said reaction cuvette; and means for monitoring the reaction of the antigen and antibody by processing light scattered from the reaction in the reaction cuvette.

22. A system for analyzing a light scattering reaction between reagents in a nephelometer, comprising:

a reaction cuvette;

means for sensing the temperature of the reaction cuvette with first temperature sensor means, the reaction cuvette being for containing the reagents during the reaction;

means for sensing the temperature of reagent with second temperature sensor means;

means for selectively increasing or decreasing the temperature of at least one of the reagents and reaction cuvette independently to maintain the temperature in a predetermined temperature range;

means for providing a range of different reaction buffers and transferring a selected reaction buffer to the reaction cuvette;

means for injecting reagents into the reaction cuvette; and means for analyzing the reaction between the reagents by processing the light scattered from the reaction in the reaction cuvette.

23. A system for analyzing a reaction between reagents in a nephelometer, comprising:

a reaction cuvette;

means for sensing the temperature of the reaction cuvette with first temperature sensor means and selectively heating or cooling the cuvette to maintain the temperature in a predetermined temperature range, the reaction cuvette being for containing the reagents during the reaction;

means for sensing the temperature of reagents with second temperature sensor means, the reagents being delivered by a reagent delivery means for injecting at least one reagent into the reaction cuvette and selectively increasing or decreasing the temperature of the reagents independently of the cuvette to maintain the temperatures in a predetermined temperature range;

means for providing a range of different buffers and transferring a selected reaction buffer to the reaction cuvette via the reagent delivery means;

means injecting an antigen reagent and an antibody reagent into the reaction cuvette for containing the reagents during the reaction wherein the means for injecting the reagents, includes:

(a) means for aspirating a selected antigen reagent sample into a sample probe from a sample pick up station, (b) means for transporting said sample from said sample pick up station to said reaction cuvette, (c) means for aspirating an antibody reagent from an antibody pick up station into an antibody probe means, and (d) means for transporting the antibody from the antibody pick up station in said reaction cuvette; and means for monitoring the reaction of the antigen and antibody by processing light scattered from the reaction in the reaction cuvette.

24. A system for analyzing a light scattering reaction between reagents in a nephelometer, comprising:

a reaction cuvette;

means for sensing the temperature of the reaction cuvette with first temperature sensor means, the reaction cuvette being for containing reagents during the reaction;

means for sensing the temperature of reagents with a second temperature sensor means, the reagents being delivered by a reagent delivery means for injecting reagents to the reaction cuvette;

means for selectively increasing or decreasing the temperature of at least one of the reagents and the reaction cuvette independently of the other;

means for providing a range of different diluents to a sample reagent and establishing different concentrations of sample reagent;

means for providing a range of different buffers and transferring a selected reaction buffer to the reaction cuvette;

means for injecting selected reagents into the reaction cuvette; and means for analyzing the reaction between the reagents by processing the light scattered from the reaction in the reaction cuvette.

* * * * *

UNITED STATES PATENT AND TRADEMARK OFFICE
CERTIFICATE OF CORRECTION

PATENT NO. : 5,296,195
DATED : March 22, 1994
INVENTOR(S) : Pang, et al.

It is certified that error appears in the above-indentified patent and that said Letters Patent is hereby corrected as shown below:

The Title Page, Section [75] Inventors: should read as follows:

Wing S. Pang, West Covina; Dobson M. Okawa, Anaheim; Peter Kan, Fullerton; George K. Shibata, Chino, all of Calif.

Signed and Sealed this

Ninth Day of August, 1994

Attest:

BRUCE LEHMAN

*Attesting Officer*         *Commissioner of Patents and Trademarks*